US008241843B2

(12) United States Patent
Krishna et al.

(10) Patent No.: US 8,241,843 B2
(45) Date of Patent: Aug. 14, 2012

(54) METHODS FOR REGULATING COMPLEMENT CASCADE PROTEINS USING ASTROVIRUS COAT PROTEIN AND DERIVATIVES THEREOF

(75) Inventors: Neel K. Krishna, Norfolk, VA (US); Kenji Cunnion, Norfolk, VA (US)

(73) Assignee: Eastern Virginia Medical School, Norfolk, VA (US)

(*) Notice: Subject to any disclaimer, the term of this patent is extended or adjusted under 35 U.S.C. 154(b) by 412 days.

(21) Appl. No.: 12/304,717

(22) PCT Filed: May 25, 2007

(86) PCT No.: PCT/US2007/012617
§ 371 (c)(1),
(2), (4) Date: Nov. 18, 2009

(87) PCT Pub. No.: WO2007/145806
PCT Pub. Date: Dec. 21, 2007

(65) Prior Publication Data

US 2010/0055106 A1 Mar. 4, 2010

Related U.S. Application Data

(60) Provisional application No. 60/813,685, filed on Jun. 15, 2006.

(51) Int. Cl.
*C12Q 1/56* (2006.01)
*A61K 39/395* (2006.01)

(52) U.S. Cl. ........................................ 435/5; 424/201.1

(58) Field of Classification Search ........................ None
See application file for complete search history.

(56) References Cited

U.S. PATENT DOCUMENTS

| | | | | |
|---|---|---|---|---|
| 6,696,562 | B1 | 2/2004 | Schultz-Cherry et al. | |
| 7,381,524 | B2 * | 6/2008 | Schultz-Cherry et al. | 435/5 |

FOREIGN PATENT DOCUMENTS

| | | | |
|---|---|---|---|
| WO | WO-9426902 | A1 | 11/1994 |
| WO | WO-9944625 | A1 | 9/1999 |
| WO | WO-0043027 | A1 | 7/2000 |
| WO | WO-2005023195 | A2 | 3/2005 |
| WO | WO-2005023296 | A1 | 3/2005 |

OTHER PUBLICATIONS

Caballero et al. Journal of Virology, 2004, vol. 78, No. 23, pp. 13285-13292.*

Knhno et al. Jarman 2000, vol. 11,(2), pp. 87-91.*

Bass et al. "Proteolytic processing of the astrovirus capsid," J. of Virol. 74(4): 1810-1814 (Feb. 2000) (5 pages).

Bass et al. "Characterization of human serotype 1 astrovirus-neutralizing epitopes," J. of Virol. 71(11): 8666-8671 (Nov. 1997) (6 pages).

Bonaparte et al. "Human astrovirus coat protein inhibits serum complement activation via C1, the first component of the classical pathway," J. of Virol. 82(2): 817-827 (Jan. 2008) (11 pages).

Caballero et al. "Structural requirments of astrovirus virus-like particles assembled in insect cells," J. of Virol. 78(23): 13285-13292 (Dec. 2004) (8 pages).

Cooper, N. "The classical complement pathway: activation and regulation of the first complement component[1]," Adv. in Immunol. 37: 151-216 (1985) (66 pages).

Dong et al. "Particle polymorphism caused by deletion of a peptide molecular switch in a quasiequivalent icosahedra virus," J. of Virol. 72(7): 6024-6033 (Jul. 1998) (10 pages).

Fogh et al. "Human tumor cells in vitro," Plenum Press, 115-159 (1975) (47 pages).

Geigenmüller et al. "Construction of a genome-length cDNA clone for human astrovirus serotype 1 and synthesis of infectious RNA transcripts," J. of Virol. 71(2): 1713-1717 (Feb. 1997) (5 pages).

Krishna, N. "Identification of structural domains involved in astrovirus capsid biology," Virol. Immunol. 18(1): 17-26 (2005) (10 pages).

Morgan et al. "Complement therapeutics: history and current progress," Molec. Immunol. 40: 159-170 (2003) (12 pages).

PCT/US07/12617 International Search Report mailed Jun. 4, 2008 (4 pages).

Sambrook et al. "Molecular cloning: a laboratory manual, 3rd ed," Cold Spring Harbor Laboratory Press (2001) (2 pages).

Schneemann et al. "Use of recombinant baculoviruses in synthesis of morphologically distinct viruslike particles of flock house virus, a nodavirus," J. of Virol. 67(5): 2756-2763 (May 1993) (8 pages).

Vaughn et al. "The establishment of two cell lines from the insect *Spodoptera frugiperda* (Lepidoptera: Noctuidae)," In Vitro, 13(4): 213-217 (1977) (5 pages). Willcocks et al. "Growth and characterization of human faecal astrovirus in a continuous cell line," Arch. Virol. 113: 73-81 (1990) (9 pages).

Younger et al. "Systemic and lung physiological changes in rats after intravascular activation of complement," J. Appl. Physiol. 90: 2289-2295 (2001) (7 pages).

EP Patent Application No. 07809212 Supplementary European Search Report (search completed Aug. 27, 2010) (2 pages).

Favoreel et al. "Virus complement evasion strategies." Journal of General Virology, 84:1-15 (2003) (15 pages).

Hair et al. "Human astrovirus coat protein binds C1q and MBL and inhibits the classical and lectin pathways of complement activation." Molecular Immunology, 47:792-798 (2010) (7 pages).

Krishna et al. "Human astrovirus coat protein: a novel C1 inhibitor." Springer Science+Business Media, LLC (2008) (15 pages).

Eastern Virginia Medical School, "Research could lead to way to halt deadly immune response." Published by ScienceDaily (Available online at http://www.sciencedaily.com/releases/2010/02/100209183127.htm) (Feb. 10, 2010) (2 pages).

* cited by examiner

*Primary Examiner* — Bao Li
(74) *Attorney, Agent, or Firm* — Wilmer Cutler Pickering Hale and Dorr LLP

(57) ABSTRACT

The present invention provides a method for modulating the complement cascade by depleting the plasma of the functional activity of complement proteins and thereby reducing or eliminating complement-mediated cell lysis. The invention provides a method for the therapeutic use of coat proteins and derivatives thereof from the Astroviradae family of viruses in the treatment of complement-mediated cell lysis and peptide mediators of inflammation. The invention provides a method for the therapeutic use of coat proteins and derivatives thereof from the Astroviradae family of viruses in the treatment of complement-mediated diseases. Methods are described herein where complement cascade, triggered by either the classical or alternative complement pathways, is prevented from effecting cell lysis and inflammation due to inhibition or depletion of one or more complement components in the serum following administration of astrovirus coat proteins or derivatives.

22 Claims, 16 Drawing Sheets

METHODS FOR REGULATING COMPLEMENT CASCADE PROTEINS USING ASTROVIRUS COAT PROTEIN AND DERIVATIVES THEREOF

RELATED APPLICATIONS

This application is a §371 of PCT/US07/12617 filed May 25, 2007 which claims priority to U.S. Provisional Application No. 60/813,685 filed Jun. 15, 2006.

STATEMENT REGARDING FEDERALLY SPONSORED RESEARCH

This invention was made with government support under Grant R21 AI060874 awarded by National Institutes of Health (NIH). The government has certain rights in the invention.

FIELD OF THE INVENTION

The invention relates generally to the field of therapeutic intervention in inflammatory and autoimmune disease. More specifically, the invention relates to prevention and treatment of complement-mediated tissue damage, and to viral illness relating to astrovirus infection.

BACKGROUND OF THE INVENTION

Astroviruses are small, non-enveloped icosahedral viruses with a single-stranded, messenger-sense RNA genome and are known to infect both mammals and birds. They are estimated to cause 2-17% of children's diarrheal illness worldwide. Astroviral infection can be especially devastating for children with malnutrition, intestinal parasites, or both. Even in developed western countries human astrovirus (HAstV) causes a significant economic loss due to parents taking time off from work to care for sick children. This trend of economic loss is likely to worsen as increasing numbers of mothers enter the workforce. Prevention or treatment of astrovirus infection in children would have a significant economic impact on physician and emergency department visits and lost workdays. In poultry farming, turkey astrovirus has a major economic impact on the turkey farming industry. In particular, turkey astroviruses cause a rapidly fatal viremic sepsis in young turkeys suggestive of overwhelming immunologic cascade that likely involves, and may be driven by, the complement system. Veterinary therapeutics designed to prevent or mitigate the damage of turkey astrovirus would be a significant development for this industry.

There is a great need for complement inhibitors. Currently, no anti-complement therapies are approved for use in humans, despite the known morbidity and mortality associated with complement disregulation in many disease processes, including such autoimmune diseases as systemic lupus erythematosus, myasthenia gravis, and multiple sclerosis. The impact of complement-mediated tissue injury in such a diverse array of diseases has driven the development of many complement inhibitors with an estimated market of between $2-4 billion annually. For a review on complement therapeutics as of 2003, please see the review article by B. P. Morgan and C. L. Harris entitled, "Complement therapeutics; history and current progress" (B. P Morgan and C. L. Harris, 2003. *Molec. Immunol.* 40, 159-170). The astrovirus coat protein appears to have extremely strong effects on the complement system, suggesting that the 'active' portion of the protein may have clinical utility in decreasing tissue damage from complement-mediated diseases. There are currently no commercially available anti-complement specific immunomodulators. There is some evidence that IVIg (intravenous immuneglobulin) in high doses has anti-complement effects that may explain its utility in some autoimmune diseases. IVIg is extremely expensive and has safety concerns because it is derived from the blood of hundreds of donors.

Current candidate compounds for anti-complement therapeutics have the significant disadvantage of acting too broadly, or in some cases are not viable due to toxicity. For example, the most powerful anti-complement substance known to date, cobra venom factor (CVF), is capable of virtually depleting all C3 in the plasma by acting as a stable C3 convertase (C3bBb). However, CVF is essentially untenable as a therapy due to the uncontrolled complement activation that results in a prolonged period of decomplementation and vulnerability to overwhelming infection in some experimental models (Younger, J. G. et al., 2001. *J. Appl. Physiol.* 90, 2289-2295). Antibody response to the CVF would likely also make the therapeutic benefit of this compound too short-lived to be ultimately useful in the treatment of chronic disease. The ideal anti-complement therapeutic method would be as effective in complement depletion as CVF but less toxic and less antigenic when administered to the host. Astrovirus coat proteins and derivatives thereof are capable of regulating complement cascade proteins to an extent comparable with CVF, and thereby are useful for treatment or prevention of complement-mediated tissue damage and mitigation of complement related diseases.

SUMMARY OF THE INVENTION

The invention relates to a method for regulating complement cascade proteins using Astroviridae family viral coat proteins and derivatives thereof, including viral coat subunits, polypeptides, peptides, fusion proteins, and chimeric derivatives of the coat protein. In one aspect of the invention, the astrovirus coat protein or derivative is used to inhibit the lytic process of the classical complement pathway by regulating classical pathway proteins. In another aspect of the invention, the coat protein or derivative is used to inhibit the lytic process triggered the alternative complement pathway by regulating alternative complement pathway proteins. In these aspects of the invention, the coat protein or derivative prevents the complement cascade from progressing through the terminal pathway of peptide complex formation. A further embodiment of this invention includes inhibiting the formation of complement pathway components such as C3 convertase, C3b, C5a, C5b, or the complex of peptides known in the art as the Membrane Attack Complex, or MAC. A person of skill in the art will recognize that testing the inhibition of the complement pathway may be achieved through well-known standard assays. In one embodiment of the invention, the assay involves using normal human serum to test lysis of sensitized red blood cells. In another embodiment of the invention, the assay involves using Factor B depleted serum in order to confine the results of the assay to testing for inhibition of the classical pathway. In a preferred embodiment of this invention, the astrovirus coat protein or derivative thereof binds to a component of the complement peptide C1.

In other embodiments of the invention, the method provides for a non-infectious virus-like particle (VLP) to regulate the activity of complement proteins. In one embodiment, multiple copies of the astrovirus coat protein or derivatives thereof are expressed on the outer surface of the particle, typically through recombinant expression of the viral coat protein in the absence of other non-structural viral genes. In another embodiment, the VLP is produced from another virus, for example Flock House virus, which displays the complement-regulating portion of the astrovirus coat protein on its surface. The method further discloses the use of peptides derived from astrovirus coat proteins for the regulation of complement and treatment of complement-related disease.

Another aspect of the invention relates to the purification of wildtype astrovirus virions or coat proteins thereof for use in regulating complement cascade proteins. Using standard viral purification techniques, wildtype astrovirus particles may be purified and used for further analysis and testing for complement regulating, inhibiting, or depleting ability.

Another aspect of the invention relates to the recombinant production of astrovirus coat protein or derivatives. A person of ordinary skill will recognize that there are many options for the production of recombinant proteins, and these methods may be adapted without undue experimentation for the purpose of producing large quantities of viral coat proteins. In a preferred embodiment of the invention, the recombinant astrovirus protein is produced in a baculovirus system. In another embodiment, the recombinant protein is produced in *E. coli*. In still further embodiments, the proteins are produced in yeast cells. In each of these cases, recombinant coat proteins thus produced are harvested from the producer cells and purified by standard protein techniques. A skilled artisan will appreciate that a wide range of eukaryotic expression systems, including mammalian cells, is available for recombinant production of proteins. A suggested reference for recombinant molecular techniques is Sambrook et al., *Molecular Cloning: A Laboratory Manual*, 3$^{rd}$ Ed., Cold Spring Harbor Laboratory Press (2001), hereby incorporated by reference. Similar references are well known to those in the art and readily available for explanations of routine recombinant molecular biology protocols.

Further embodiments of the invention include the production of recombinant proteins that include regions of a second protein fused to the astroviral coat protein or derivative. Such a fusion or chimeric protein may be used to regulate complement and decrease complement-related tissue damage at a specific target site in the recipient by linking the coat protein to an antibody or antibody fragment.

In another embodiment, the invention is further directed to the use of astrovirus coat protein or derivatives thereof to treat complement-mediated tissue damage and disease. Complement-mediated tissue damage is frequently associated with autoimmune and other diseases with inflammatory pathologies. Astrovirus coat protein or derivatives may be useful in the treatment of rheumatoid arthritis, systemic lupus erythematosus, multiple sclerosis, myasthenia gravis, hemolytic anemia, membranoproliferative glomerulonephritis, serum sickness, Adult Respiratory Distress Syndrome, ischemia-reperfusion injury (for example, stroke or myocardial infarction), allo- or xeno-transplantation (including hyperacute rejection and Graft Versus Host Disease), Alzheimer's Disease, burn injuries, hemodialysis damage, cardiobypass damage, Paroxysmal Nocturnal Hemoglobinuria, and other diseases associated with complement-mediated tissue damage. Further uses include veterinary application to treat animal diseases, such as turkey astrovirus infection.

In another embodiment, the invention is directed towards methods for isolating and purifying astrovirus coat protein by producing coat protein or derivatives thereof or VLPs to generate a vaccine against astrovirus infection in humans or animals.

The present invention provides pharmaceutical compositions comprising at least one astrovirus coat protein or derivatives thereof, and one or more pharmaceutically acceptable carriers, diluents, or excipients. In one embodiment, the composition comprises a therapeutically effective amount of the astrovirus coat protein or derivatives thereof. In another embodiment, the composition comprises at least one other active ingredient effective in treating at least one disease associated with complement-mediated tissue damage.

The present invention also provides a method of preventing or treating a disease associated with complement-mediated tissue damage comprising administering the pharmaceutical compositions of the present invention to an animal in need thereof. In one embodiment, the pharmaceutical composition of the present invention is administered as the sole active pharmaceutical agent. In another embodiment, it is used in combination with one or more additional therapeutic or prophylactic agent that is effective for preventing or treating the disease in question. In this aspect, the method of the present invention comprises administrating the pharmaceutical composition of the present invention before, concurrently, and/or after, one or more additional therapeutic or prophylactic agent effective in treating at least one disease associated with complement-mediated tissue damage.

Unless otherwise defined, all technical and scientific terms used herein have the same meaning as commonly understood by one of ordinary skill in the art. Although methods and materials similar or equivalent to those described herein can be used in the practice or testing of the present invention, suitable methods and materials are described below. All publications, patent applications, patents, and other references mentioned herein are incorporated by reference in their entirety. In addition, the materials, methods, and examples are illustrative only and not intended to be limiting.

Other features and advantages of the invention will be apparent from the detailed description, drawings, and from the claims.

BRIEF DESCRIPTION OF THE FIGURES

Table 1 is a listing of astrovirus family members with fully sequenced coat protein genes. Samples in bold indicate coat protein sequences identified in this study; both a unique identifier and the GenBank accession number are provided for each isolate. Abbreviations: HAstV, human astrovirus; FAstV, feline astrovirus; MAstV, mink astrovirus; PAstV, pocine astrovirus; OAstV, ovine astrovirus; ANV, avian nephritis virus; TAstV, turkey astrovirus.

Table 2 summarizes the results of RBC lysis assays on HAstV serotypes 1-4.

FIG. 12A is an image of an immunoblot using partially purified complement factor C1 and purified complement factors C2, C3, and C4 loaded into a non-reducing 7.5% SDS-PAGE gel (without boiling), electrophoresed, transferred to nitrocellulose, probed with HAstV-1 coat protein, and incubated with a primary antibody against HAstV-1 virions and an HRP-conjugated secondary antibody.

FIG. 12B is an image of the same immunoblotting procedure in FIG. 12A without using the HAstV-1 coat protein probe.

FIG. 12C is an image of an immunoblot using BSA, C1, C1q, C1r, and C1s loaded into a reducing buffer, boiled, electrophoresed on a 12% SDS-PAGE gel, and subsequently incubated with HAstV-1 coat protein and visualized as in FIG. 12A.

FIG. 12D is an image of the same blot depicted in FIG. 12C after stripping and re-blotting with polyclonal antibodies to C1q, C1r, and C1s.

FIG. 12E is an image of a duplicate blot of the experiment in FIG. 12C without using the HAstV-1 coat protein probe.

DETAILED DESCRIPTION OF THE INVENTION

Figure 1:
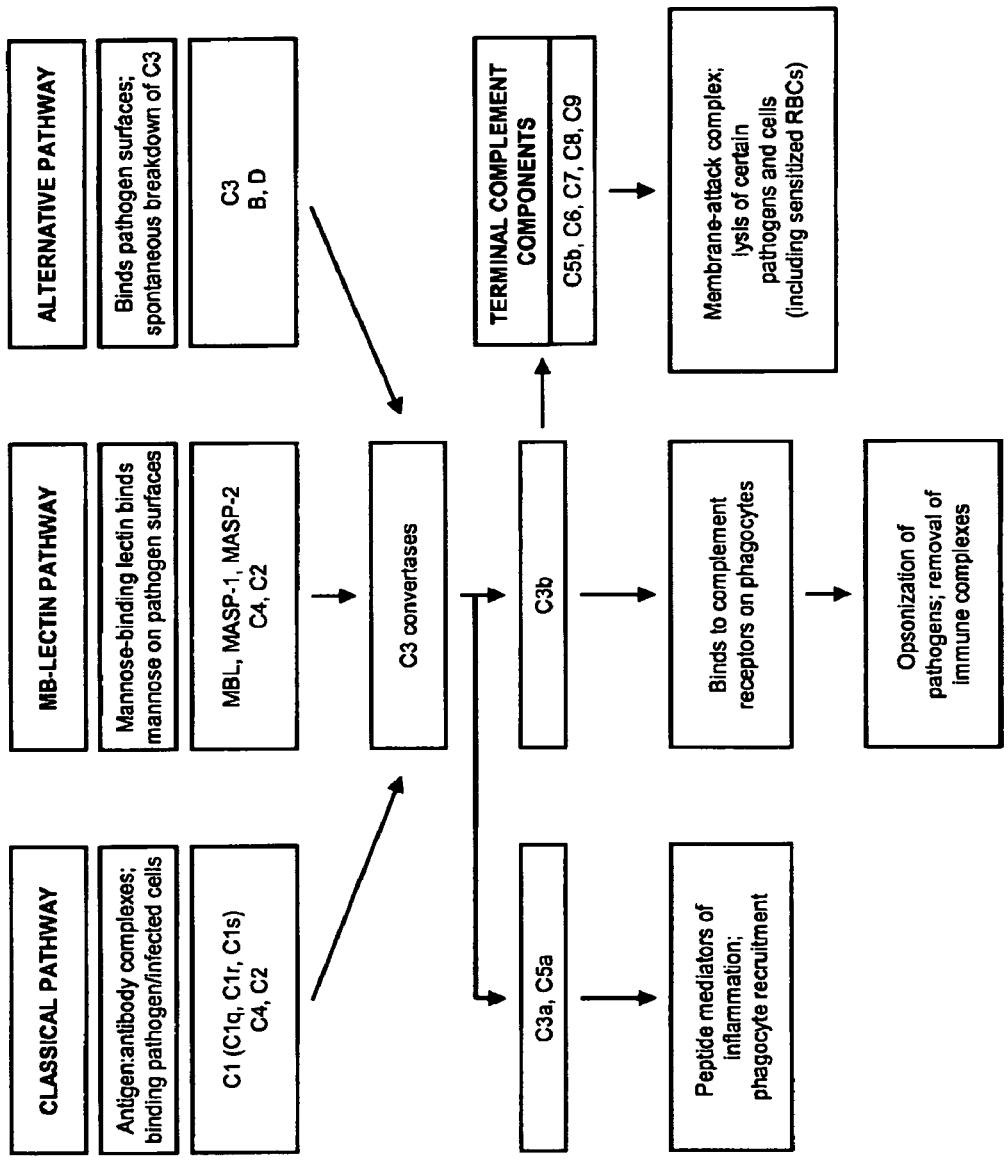
FIG. 1 is an overview of the three pathways of complement activation. The main protein factors and their effector functions are indicated.

The present invention provides methods for regulating complement cascade proteins through the use of coat protein and derivatives thereof from the viral Astroviridae family. This invention has multiple uses and advantages. Astrovirus coat proteins may be used to treat complement-mediated diseases or reduce complement-mediated tissue damage in a variety of pathologies in both humans and animals.

The Astrovirus Coat Protein

For a review of the current knowledge concerning astrovirus capsid biology, please refer to the review entitled "Identification of structural domains involved in astrovirus capsid biology" (*Viral Immunology* 18(1): 17-26, 2005), incorporated herein by reference in its entirety. Briefly, the Astroviridae constitute a family of non-enveloped, icosahedral viruses with a single-stranded, messenger-sense RNA genome. These viruses infect mammals and birds and are a significant cause of gastroenteritis in young children as well as disease in other animals and avian species, including a fatal viremic sepsis in turkeys. The invention herein discloses, for example, a method for an in vitro assembly system in which large quantities of the coat protein (and coat protein deletion mutants) can be purified using a recombinant baculovirus expression system in insect cells. Other recombinant techniques are also contemplated for the production of coat protein or derivatives. Infectious astrovirus, such as HAstV-1 or other virions produced in mammalian tissue culture, may also be used.

The Complement System

The complement system comprises a group of related plasma proteins that, when activated, generates an extremely destructive immunologic cascade. The complement system combats infection by a wide variety of methods including lysis of bacteria and infected cells by pore formation (i.e., formation of the Membrane Attack Complex or "MAC"), opsonization (immune-tagging) leading to ingestion and destruction by white blood cells, activation of white blood cells, directing white blood cells to the site of infection, stimulating B-lymphocyte responses, and antibody generation. The complement system is activated by three known pathways: the classical pathway, the alternative pathway, and the mannan-binding lectin pathway (see FIG. 1). Each results in a cascade of protein-protein reactions amplifying in an exponential manner that culminate in an extremely robust immune response. While complement is a vital host defense against pathogenic organisms such as bacteria and some enveloped viruses, its unchecked activation can cause devastating host cell damage. Host tissue damage mediated by complement has been implicated in a wide variety of diseases including autoimmune pathologies such as: rheumatoid arthritis, systemic lupus erythematosus, multiple sclerosis, myasthenia gravis, autoimmune hemolytic anemia, membranoproliferative glomerulonephritis, and serum sickness. It has also been identified as contributing to the pathogenesis of the following diseases: Adult Respiratory Distress Syndrome (ARDS), stroke (ischemia-reperfusion injury), myocardial infarction (ischemia-reperfusion injury), allo- and xenotransplantation (hyperacute rejection & graft versus host disease), Alzheimer's disease, burn injuries, hemodialysis damage, cardiopulmonary bypass damage, and Paroxysmal Nocturnal Hemoglobinuria.

Accordingly, the present invention relates to using coat proteins or derivatives thereof from the Astroviridae family of viruses to mitigate the tissue damage associated with complement cascade proteins. Although not intending to be bound by any particular mechanistic theory, the coat proteins may deplete or inhibit either the classical complement pathway, typically initiated by antibody binding to an antigen followed by the C1 protein and fragments thereof, or the alternative pathway, typically initiated by the C3 protein and fragments thereof.

As used herein, the term "astrovirus" refers to any member of the Astroviridae family, including but not limited to mammalian astrovirus species such as bovine, feline, human, ovine, porcine, and mink astrovirus, or avian species including chicken, turkey, and duck astrovirus (Table 1).

| Identifier[a] | Host/Serotype[b] | Sequence Length | | Location |
|---|---|---|---|---|
| | | Nucleotide | Amino acid | |
| L23513 | HAstV-1 | 2364 | 788 | UK |
| S68561 | HAstV-1 | 2361 | 787 | UK |
| NC_001943 | HAstV-1 | 2361 | 787 | UK |
| AY720892 | HAstV-1 | 2364 | 788 | Germany |
| 001-EF138823 | HAstV-1 | 2364 | 788 | CA, USA |
| 002-EF138824 | HAstV-1 | 2370 | 790 | OH, USA |
| 003-EF138825 | HAstV-1 | 2364 | 788 | OH, USA |
| 004-EF138826 | HAstV-1 | 2364 | 788 | OH, USA |
| L06802 | HAstV-2 | 2391 | 797 | UK |
| 005-EF138827 | HAstV-2 | 2400 | 800 | CA, USA |
| AF141381 | HAstV-3 | 2385 | 795 | Germany |
| AF117209 | HAstV-3 | 2385 | 795 | USA |
| 006-EF138828 | HAstV-3 | 2385 | 795 | CA, USA |
| 007-EF138829 | HAstV-3 | 2385 | 795 | OH, USA |
| DQ070852 | HAstV-4 | 2316 | 772 | Brazil |
| AB025801 | HAstV-4 | 2316 | 772 | Japan |
| AB025802 | HAstV-4 | 2316 | 772 | Japan |
| AB025803 | HAstV-4 | 2316 | 772 | Japan |
| AB025804 | HAstV-4 | 2316 | 772 | Japan |
| AB025805 | HAstV-4 | 2316 | 772 | Japan |
| AB025806 | HAstV-4 | 2316 | 772 | Japan |
| AB025807 | HAstV-4 | 2316 | 772 | Japan |
| AB025808 | HAstV-4 | 2316 | 772 | Japan |
| AB025809 | HAstV-4 | 2316 | 772 | Japan |
| AB025810 | HAstV-4 | 2316 | 772 | Japan |
| AB025811 | HAstV-4 | 2316 | 772 | Japan |
| AB025812 | HAstV-4 | 2316 | 772 | Japan |
| AY720891 | HAstV-4 | 2316 | 772 | Germany |
| DQ344027 | HAstV-4 | 2316 | 772 | China |
| Z33883 | HAstV-4 | 2316 | 772 | UK |
| DQ028633 | HAstV-5 | 2352 | 784 | Brazil |
| AB037273 | HAstV-5 | 2352 | 784 | Japan |
| AB037274 | HAstV-5 | 2352 | 784 | Japan |
| U15136 | HAstV-5 | 2352 | 784 | UK |
| AB013618 | HAstV-6 | 2337 | 779 | Japan |
| AB031030 | HAstV-6 | 2337 | 779 | Japan |
| AB031031 | HAstV-6 | 2337 | 779 | Japan |
| Z46658 | HAstV-6 | 2337 | 779 | UK |
| Y08632 | HAstV-7 | 2376 | 792 | Norway |
| AF248738 | HAstV-7 | 2376 | 792 | South Africa |
| Z66541 | HAstV-8 | 2349 | 783 | UK |
| AF260508 | HAstV-8 | 2349 | 783 | Mexico |
| 008-EF138830 | HAstV-8 | 2349 | 783 | OH, USA |
| 009-EF138831 | HAstV-8 | 2349 | 783 | OH, USA |
| AF056197 | FAstV | 2451 | 817 | UK |
| NC_004579 | MAstV | 2328 | 776 | Sweden |
| AB037272 | PAstV | 2331 | 777 | Japan |
| Y15938 | PAstV | 2352 | 784 | Japan |
| NC_002469 | OAstV | 2289 | 763 | Scotland |
| NC_003790 | ANV | 2052 | 684 | Japan |
| AB046864 | ANV-2 | 2040 | 680 | Japan |
| AY769615 | TAstV-2 | 2166 | 722 | USA |
| NC_005790 | TAstV-2 | 2175 | 725 | USA |
| AY769616 | TAstV-3 | 2175 | 725 | USA |
| NC_002470 | TAstV | 2016 | 672 | USA |

The term "coat protein" refers to components of the astrovirus capsid, including but not limited to intact or assembled astrovirus protein coat or subunits thereof, precursor proteins, epitopes, monomers, dimers, trimers, oligomers, polypeptides, or peptides.

The term "derivative" refers to components of the astrovirus coat, either purified from wildtype virus or recombinantly produced, which are partial regions or modifications of the astrovirus coat protein such as isolated coat subunits, truncation or deletion mutants, substitution mutants, chimeric proteins, fusion proteins, or other proteins containing elements of the astrovirus coat in whole or part, in which the derivative is capable of regulating complement cascade protein activity.

The terms "complement cascade" and "complement protein" refer to complement proteins C1-C9 and subunits thereof, including but not limited to C1q, C1r, C1s, C4a, C4b, C2a, C2b, C3a, C3b, Factor B, Ba, Bb, C3 convertase, C5 convertase, D, Properdin, C5a, C5b, C6, C7, C8, C9, or combinations thereof in the classical, alternative, or mannan-binding lectin complement pathway as would be appreciated by one of skill in the art.

The term "inhibition" refers to the reduction in the biological function of an enzyme, protein, peptide, factor, byproduct, or derivative thereof either individually or in complexes; reduction in the quantity of a biological protein, peptide, or derivative thereof whether in vivo or in vitro; or interruption of a biological chain of events, cascade, or pathway known to comprise a related series of biological or chemical reactions. The term inhibition may thus be used, for example, to describe the reduction of quantity of a single component of the complement cascade compared to a control sample, a reduction in the rate or total amount of formation of a component or complex of components, or the reduction of the overall activity of a complex process or series of biological reactions leading to such outcomes as cell lysis, formation of convertase enzymes, formation of complement-derived membrane attack complexes, inflammation, or inflammatory disease. In an in vitro assay, the term "inhibition" may refer to the measurable reduction of some biological or chemical event, but the person of ordinary skill in the art will appreciate that the measurable reduction need not be total to be "inhibitory."

Production of Viral Coal Protein

Numerous sources for the production or isolation of astrovirus coat protein and derivatives thereof are well understood in the art. Examples of viral coat protein purification techniques include the use of sucrose gradient sedimentation as well as separation columns, which may purify viral particles based on size exclusion, affinity binding, ion exchange, hydrophobic interaction (H1C), or other means. In some cases, modified coat proteins or derivative proteins may be difficult to purify to homogeneity using a column. In these circumstances, the artisan of ordinary skill will appreciate that alternative methods of purification, such as electrophoresis followed by elution and recovery from the gel is an alternative means for preparation of purified viral coat proteins.

In another aspect of the invention, it is contemplated that recombinant technology may be employed to produce astroviral coat proteins. In a preferred embodiment of this aspect of the invention, a recombinant baculovirus is used for in vitro viral coat protein production. Sf9, Sf21, or Tini/High5 insect cells are commonly used in this technique to generate baculovirus stocks, which subsequently are used to infect producer cells, which in turn generate the recombinant coat protein. Using such a technique or a variation thereof allows for the large-scale production of both wildtype astrovirus coat protein in addition to recombinant mutants, chimeric proteins, fusion proteins, and virus-like particles. Provided herein by way of example infra are methods for the production and purification of HAstV-1 (Newcastle) full length coat protein Ac_1-787, deletion mutant Ac_1-415, and deletion mutant Ac_416-787. Other variations of coat protein mutants may similarly be produced and purified in a similar fashion.

The term "virus like particles" (VLP) refers to non-infectious viral particles or capsids, which may be produced by recombinant means or through the use of chimeric technology in conjunction with VLP from other viruses that display astrovirus coat protein epitopes or regions in a polyvalent manner on the particle surface.

As used herein, the term "chimeric" or "fusion" coat protein is intended to include any recombinant protein capable of inhibiting or depleting complement cascade factors which includes a constituent polypeptide, component, or region of the astrovirus coat protein in addition to at least one region from a second polypeptide or protein, such as an antibody or antibody fragment.

In another embodiment of the invention, the production of recombinant astrovirus coat proteins or derivatives thereof takes place in E. coli cells using standard recombinant genetic techniques as will be appreciated by one of skill in art. Astrovirus coat peptides, polypeptides, regions, or whole proteins thus produced are then subsequently purified on a sucrose gradient, column or similar apparatus as discussed supra. It will be recognized by one of ordinary skill in the art that production of recombinant proteins is readily adaptable to other systems, such as yeast cells, which likewise involves the introduction of recombinant DNA into host cells followed by propagation, lysis, and purification of the protein of interest.

Inhibition of Complement-mediated Lysis by Astrovirus Coat Protein

The invention disclosed herein demonstrates by way of example that the coat protein of Astroviridae family member HAstV-1 is as effective as CVF in inhibiting complement-mediated cell lysis. Given the structural similarities between members of the Astroviridae family, coat protein or derivatives thereof from other mammalian strains of astrovirus, such as human strains HAstV-2 through HAstV-8, bovine, porcine, ovine, feline, mink and poultry strains such as chicken, turkey, and duck astrovirus are contemplated herein as also having anti-complement activity. Table 1 provides a non-limiting list of fully sequenced astrovirus family members to date.

In order to compare the complement-depleting or inhibiting activity of HAstV-1 or other astrovirus coat protein to CVF, it is informative to test the astrovirus coat protein in a series of cell lysis experiments as described in the examples infra. Red blood cells are a sensitive and specific method for testing serum complement activation by measuring red blood cell lysis. Measurement of the percentage of lysed cells in the assay is therefore a proximal measurement of complement activation in the experimental sample, typically normal human serum (NHS). The method disclosed herein for inhibiting complement mediated lysis is comparable in efficacy to CVF, the strongest complement-depleting substance in nature. The inhibition of complement-mediated lysis of RBCs applies not only to purified coat protein, but also to intact HAstV-1 virions. Accordingly, in another embodiment of the invention, intact astrovirus virions or virus-like particles are used to deplete complement cascade proteins from the plasma. Although HAstV-1 virions and purified coat protein demonstrate similar levels of complement suppression when compared to CVF, the data presented here demonstrates that astrovirus virions and coat protein act to suppress serum complement activity through an inhibition mechanism as opposed to activation and subsequent depletion of complement factors exhibited by CVF.

It is important to note that wildtype astrovirus coat protein often oligomerizes into trimers (and possibly other higher order oligomers) in the buffer in which the coat protein is stored. Thus, it is contemplated that, in one aspect of the invention, the coat protein in the red blood cell assays for complement-mediated lysis is a dimer, a trimer, or a higher-ordered oligomer. The coat protein may precipitate when exposed to calcium ions, an effect which occurs to a lower extent with magnesium and not at all with EDTA/NaCl. It is contemplated that these observations may be indicative of early viral-like particle assembly, as many icosahedral capsids require calcium ions for assembly. The RBC lysis assays described herein contain calcium ions (150 micromolar) and would therefore be consistent with the observed self-assembly of the coat protein subunits.

Interactions Between Protein Coat Subunits and Complement Components

An important area of investigation for the optimization of using the invention disclosed herein is to identify interactions between specific complement components and astrovirus coat proteins. This may be achieved, for example, through the use of a modified viral overlay blot, described by way of example infra., which generally involves electrophoretic gel separation of complement proteins followed by transfer to a membrane and probing with purified coat protein. Several caveats should be noted in this approach. First, the artisan of ordinary skill will appreciate that while complement proteins C2, C3, and C4 are readily available as highly purified preparations, the C1 protein complex is much more difficult to purify owing to the fact that it is a very labile complex and falls apart easily. As a result, other serum proteins are usually present in C1 preparations. However, C1 preparations that are free of other complement factors such as C2, C3, C4, and C5, and routine batch testing with anti-complement antibodies is generally sufficient to prevent most cross-contamination with other complement factors.

While C1q, a complex molecule, separates into several fragments during electrophoresis, C1r and C1s run as homodimers in non-reducing gels. Binding of the astrovirus coat protein in these assays may be specific to homodimers; one of ordinary skill will realize that the same protein preparations run under reducing conditions may not reflect binding at all, either because the coat protein is incapable of binding the monomer or because the concentration of the monomer in the preparation is below detectable levels.

Formulation and Administration

The present invention provides pharmaceutical compositions comprising at least one astrovirus coat protein or derivatives thereof, and one or more pharmaceutically acceptable carriers, diluents, or excipients. Pharmaceutically acceptable carriers, excipients, or stabilizers are nontoxic to recipients at the dosages and concentrations employed. They can be solid, semi-solid, or liquid. Thus, the pharmaceutical compositions of the present invention can be in the form of tablets, pills, powders, lozenges, sachets, cachets, elixirs, suspensions, emulsions, solutions, or syrups.

Some examples of pharmaceutically acceptable carriers, diluents, or excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The pharmaceutical compositions of the present invention can be formulated so as to provide quick, sustained or delayed release of the active ingredient after administration by employing procedures known in the art.

The pharmaceutical compositions of the present invention are prepared by mixing the astrovirus coat protein or derivatives having the appropriate degree of purity with pharmaceutically acceptable carriers, diluents, or excipients. Examples of formulations and methods for preparing such formulations are well know in the art. See, e.g., Remington's Pharmaceutical Sciences, 18th edition (1995), hereby incorporated by reference.

The pharmaceutical compositions of the present invention are useful as a prophylactic and therapeutic agent for various disorders and diseases as set forth above. In one embodiment, the composition comprises a therapeutically effective amount of the astrovirus coat protein or derivatives thereof. In another embodiment, the composition comprises at least one other active ingredient effective in treating at least one disease associated with complement-mediated tissue damage. The term "therapeutically effective amount," as used herein, refers to the total amount of each active component that is sufficient to show a meaningful patient benefit.

The therapeutically effective amount of the astrovirus coat proteins or derivatives vary depending on such factors as the condition being treated, the severity of the condition, the time of administration, the route of administration, the rate of excretion of the compound employed, the duration of treatment, the co-therapy involved, and the age, gender, weight, and condition of the patient, etc. Determining therapeutically effective amount is well within the skill of a practicing physician. Accordingly, it may be necessary for the therapist to titer the dosage and modify the route of administration as required to obtain the maximal therapeutic effect.

Under such guidelines, the effective daily dose generally is within the range of from about 0.001 to about 100 milligrams per kilogram of body weight, preferably about 0.01-50 mg/kg, more preferably about 0.1-20 mg/kg. This can be achieved through a 1-6 times daily dosing regimen. Alternatively, optimal treatment can be achieved through sustained release at a less frequent dosing regimen.

Pharmaceutical formulations may be adapted for administration by any appropriate route, for example by the oral, nasal, topical (including buccal, sublingual, or transdermal), or parenteral (including subcutaneous, intracutaneous, intramuscular, intraarticular, intraperitoneal, intrasynovial, intrasternal, intrathecal, intralesional, intravenous, or intradermal injections or infusions) route. For human administration, the formulations preferably meet sterility, pyrogenicity, general safety, and purity as required by FDA Office and Biologics standards.

Combination Therapies

The present invention also provides a method of preventing or treating a disease associated with complement-mediated tissue damage comprising administering the pharmaceutical compositions of the present invention to an animal in need thereof. While the pharmaceutical compositions of the present invention can be administered as the sole active pharmaceutical agent, they can also be used in combination with one or more additional therapeutic or prophylactic agent that is effective for preventing or treating the disease in question. In this aspect, the method of the present invention comprises administrating the pharmaceutical composition of the present invention before, concurrently, and/or after, one or more additional therapeutic or prophylactic agent effective in treating at least one disease associated with complement-mediated tissue damage.

For example, the pharmaceutical compositions of the present invention can be used to treat rheumatoid arthritis, either alone or in combination with a non-steroidal anti-inflammatory agent (NSAID), a corticosteroid, or a disease modifying anti-rheumatic drug (DMARD).

Examples of NSAID include Salicylates (such as Aspirin, Amoxiprin, Benorilate, Choline magnesium salicylate, Diflunisal, Faislamine, Methyl salicylate, Magnesium Salicylate, and Salicyl salicylate (salsalate)), Arylalkanoic acids (such as Diclofenac, Aceclofenac, Acemetacin, Bromfenac, Etodolac, Indometacin, Ketorolac, Nabumetone, Sulindac, and Tolmeti), 2-Arylpropionic acids (such as Ibuprofen, Carprofen, Fenbufen, Fenoprofen, Flurbiprofen, Ketoprofen, Loxoprofen, Naproxen, Tiaprofenic acid, and Suprofen), N-Arylanthranilic acids (such as Mefenamic acid and Meclofenamic acid), Pyrazolidine derivatives (such as Phenylbutazone, Azapropazone, Metamizole, Oxyphenbutazone, and Sulfinprazone), Oxicams (such as Piroxicam, Lornoxicam, Meloxicam, and Tenoxicam), COX-2 Inhibitors (such as Etoricoxib, Lumiracoxib, and Parecoxib), Sulphonanilides such as Nimesulide, and others such as Licofelone and Omega-3 Fatty Acids.

Examples of corticosteroid include triamcinolone (Aristocort®), cortisone (Cortone® Acetate Tablets), dexamethasone (Decadron® Elixir), prednisone (Deltasone®), and methylprednisolone (Medrol®), Examples of DMARD include methotrexate (Rheumatrex®), leflunomide (Arava®), etanercept (Enbrel®), infliximab (Remicade®), adalimumab (Humira®), anakinra (Kineret®), sulfasalazine (Azulfidine EN-Tabs®), antimalarials, gold salts, d-penicillamine, cyclosporin A, cyclophosphamide and azathioprine.

Soliris™ (eculizumab) is a humanized anti-C5 monoclonal antibody. It has been approved by the FDA for the treatment of the rare form of hemolytic anemia, paroxysmal nocturnal hemoglobinuria. In one embodiment, the pharmaceutical compositions of the present invention can be used in combination with Soliris™ in treating paroxysmal nocturnal hemoglobinuria, heart disease, pulmonary diseases, autoimmune diseases, asthma, as well as the ancillary care of transplant.

The pharmaceutical compositions of the present invention can be administered with the additional agent(s) in combination therapy, either jointly or separately, or by combining the pharmaceutical compositions and the additional agent(s) into one composition. Dosage administration and adjustment is done to achieve maximal management of the conditions to be treated. For example, both the pharmaceutical compositions and the additional agent(s) are usually present at dosage levels of between about 10 and about 150%, more preferably, between about 10 and about 80% of the dosage normally administered in a monotherapy regimen.

Hereditary angioedema (HAE) is a very rare genetic disorder caused by reduced levels or non-functional C1-inhibitor. C1-inhibitor naturally regulates C1 activation and treatment of acute edema in these patients requires substantial infusion of C1-inhibitor or plasma transfusion. Because astrovirus coat protein functionally blocks C1 activation, this would be a potential therapy and would fill a therapeutic need because C1-inhibitor has to be purified from human sera from multiple subjects and therefore has the potential to contaminated with human bloodborne pathogens. Therapeutic administration of astrovirus coat protein or a derivative thereof may potentially be used to inhibit C1 either in adjunct therapy with C1-inhibitor or as a stand-alone therapeutic treatment.

EXAMPLES

The invention is further illustrated by the following examples. The examples are provided for illustrative purposes only. They are not to be construed as limiting the scope or content of the invention in any way.

Example 1

Cell Lines and Viruses

For baculovirus production of astrovirus coat protein, *Spodoptera Frugiperda* cells (line IPLB-Sf21) (Vaughn, J. L. et al., 1977. *In vitro*. 13, 213-217) were propagated in TC100 medium supplemented with 10% heat-inactivated FBS as described previously (Scheneemann, A. et al., 1993. *J. Virol.*

67, 2756-2763). Virus stocks of the recombinant baculoviruses encoding the wildtype HAstV-1 coat protein gene and deletion mutants were prepared by infecting Sf21 cells at a multiplicity of infection (MOI) of 1 in cell growth medium and allowing the infection to proceed for 5 to 7 days. Following the infection period, cell debris was removed in a low speed spin and virus contained in the medium was titered by plaque assay and stored at 4° C.

For propagation of infectious astrovirus particles, CaCo-2 cells (J. Fogh and G. Trempe, 1975. New human tumor cell lines. In: Fogh J (ed) *Human tumor cell lines in vitro*. Plenum, New York, pp 115-159) were propagated in minimum essential medium with 10-20% heat-inactivated FBS according to instructions (ATCC). A cell-adapted strain of HAstV-1 (Oxford) (kindly provided by Dr. D. K. Mitchell, Eastern Virginia Medical School, Norfolk, Va., USA) was propagated in CaCo2 cells (Willcocks, M M. et al., 1990. *Arch. Virol.* 113: 73-81). Briefly, cell monolayers in minimum essential medium lacking FBS were infected with a viral inoculum containing 10 μg/ml of trypsin type IX (Sigma) and virus was allowed to adhere for 1 h at 37° C. The inoculum was removed and medium containing 2 μg/ml of trypsin was added; cells were then incubated for approximately 48 hours at 37° C. Following incubation, viral suspensions were released from the cells by 3 cycles of freeze/thaw. Cell debris was then removed in a low speed spin and the supernatant containing virus was aliquoted and stored at −80° C. Cell-adapted strains of HAstV types 2-7, previously propagated as above, were provided by Dr. D. K. Mitchell.

Example 2

Real-Time Reverse Transcription PCR

To quantify HAstV stocks, a real-time PCR method was developed. To isolate total RNA, 40 μL of CaCo2 cells lysates infected with HAstV-1 were diluted 1:5 in 1× minimum essential medium. RNA was then extracted using Trizol (Invitrogen) per manufacturer's instructions. Following isolation, RNA was treated with DNAseI (Promega) for 30 min at 37° C. and the enzyme was then inactivated at 65° C. for 10 min. RNA was stored at −80° C.

One-step real-time RT-PCR was performed using the iCycler IQ™ system (Bio-Rad). The real-time RT-PCR reaction was assembled using the Superscript III Platinum Syber Green® 1-Step qRT-PCR kit (Invitrogen). Briefly, a reaction mixture was made, containing 12.5 μL 2× Syber® Green RT-PCR Reaction Mix, 0.5 μL each of 10 μM forward primer ORF1a-F1 and reverse primer ORF1a-R1 (targeting a conserved portion of the serine protease gene of the HAstVs, 200 nM final concentration), 0.5 μL iScript Reverse Transcriptase for One-Step RT PCR, 6.0 μL sterile water and 5.0 μL of the total RNA (isolated as described above). cDNA synthesis was achieved by incubating the reaction for 10 min at 50° C., followed by inactivation of iScript RT at 95° C. for 5 min. PCR cycling and detection included 45 cycles of incubation at 95° C. for 10 sec, 55° C. for 30 sec, and 72° C. for 30 sec, respectively. For the melt curve, samples were incubated at 95° C. for 1 min, 57° C. for 1 min, followed by 80 cycles of incubation for 10 sec, starting at 57° C., and increasing at 0.5° C. increments with each successive cycle. To generate a standard curve, an RNA standard was prepared by T7-mediated in vitro transcription (Ambion) of a genome-length cDNA clone (pAVIC) for HAstV-1 (U. Geigenmüller, et al. 1997. *J. Virol.* 71, 1713-1717.). The RNA standard was serially diluted from $10^{10}$ to $10^0$ and the standard curve was established by plotting the threshold cycle vs. log starting copy number for each dilution. Log starting copy number of the viral RNA contained in the CaCo2 cell lysate was then extrapolated from the equation of the standard curve line, Y=mX+b, where Y=threshold cycle ($C_T$), m=slope of the standard curve line, X=log starting copy number, b=Y-intercept or threshold fluorescence value.

Example 3

Construction of Recombinant Baculoviruses

Recombinant baculoviruses containing full-length (Ac_1-787) and deletion mutants (Ac_1-415 and Ac_416-787) of the HAstV-1 (Newcastle) coat protein gene were generated with the BacPAK baculovirus expression system kit (Clontech). To this end, the DNA fragment encoding the cDNA of the coat protein (kindly provided by Dr. M. J. Carter, University of Surrey, England) (Willcocks, 1994) was amplified by PCR with Pfu polymerase (Stratagene) and primers harboring BamHI and XbaI restriction sites at the 5' and 3' end of the PCR product, respectively. Primers were designed to amplify the entire capsid gene coding region (aa 1-787) or the gene segments corresponding to aa 1-415 and aa 416-787. Each PCR product was then purified by agarose gel electrophoresis and the Gene clean II kit (Qbiogene), digested with BamHI and XbaI, and separately ligated into a BamHI/XbaI-digested transfer vector pBacPAK9. Following transformation of JM109 competent cells (Promega), plasmid DNA was isolated from several clones for each construct and the presence of the inserted DNA was determined by diagnostic restriction endonuclease mapping. Positive clones harboring the various coat protein gene constructs were then completely sequenced across the inserted DNA using Big Dye Terminator Sequencing Kit v 3.1 in an automated sequencing instrument (Applied Biosystems).

Generation of the recombinant baculovirus was carried out according to the manufacturer's protocols (Clontech). Briefly, transfer vector pBacPAK9, containing the HAstV-1 coat protein constructs were individually mixed with Bsu36I-linearized BacPAK6 baculovirus DNA and transfected into Sf1 cells. Three days post transfection, cell supernatants were harvested and putative recombinant viruses were isolated by plaquing the supernatants once on Sf21 cell monolayers. Individual plaque isolates were amplified and titered following confirmation of the presence and expression of the inserted gene by immunoblot analysis of the infected cell lysates (Dong X F et al., 1998. *J. Virol.* 72, 6024-6033) using a rabbit polyclonal antibody to HAstV-1 particles (kindly provided by Dr. D. M. Bass, Stanford University, USA) (D. M. Bass and U. Upadhyayula. 1997. *J. Virol.* 71, 8666-8671) and a horseradish peroxidase-conjugated goat anti-rabbit IgG secondary antibody (Pierce). Signal detection by enhanced chemiluminescence was performed on a Versadoc instrument (Bio-Rad).

Example 4

Recombinant Protein Synthesis and Isolation

Sf21 cells ($2\times10^8$) in a 50 ml conical vial were infected with the recombinant baculoviruses at a MOI of 5 per cell. After 1 h at room temperature with rocking, the infected cells were transferred to a spinner flask containing cell growth medium plus antibiotics. The spinner flasks were then allowed to stir at 27° C. Five days post infection, cells were pelleted in a low speed spin and the medium was discarded. Cell pellets were then frozen at −20° C. until needed.

The following protocol was developed to purify soluble coat protein from Ac_1-787 and Ac_1-415 infected cells. Unless otherwise indicated, all the following steps were carried out at 4° C. with pre-chilled buffers and protease inhibitors (B. D. Pharmingen). Six frozen pellets were each resuspended in 2 volumes of TNE (50 mM Tris [pH 7.0], 0.1 M NaCl, 10 mM EDTA) buffer and lysed by 3 cycles of freeze/thaw. Lysates were centrifuged for 10 min at 13,300×g, and the supernatant was discarded. The pellets, which contain aggregates of the coat protein, were each resuspended in 1 ml of TNE buffer containing 2% NP-40 and incubated on ice for 30 min. The resulting suspension was centrifuged at 13,300×g for 5 min, and the supernatant was discarded. Each pellet was resuspended in 1 ml of TNM (50 mM Tris [pH 7.0], 0.1 M NaCl, 20 mM $MgSO_4$) buffer plus 2 µl of 10 mg/ml DNase1 (Sigma), incubated 30 min at room temperature and centrifuged for 5 min at 13,000×g, after which the supernatant was discarded. The pellets were each resuspended in 1 ml of TNE buffer using a pipette tip. The individual aliquots were pooled into 2 tubes at this point and pelleted through a 1 ml 30% (wt/vol) sucrose cushion in TNE buffer at 234,000×g in a SW50.1 Ti rotor (Beckman) for 1 h at 4° C. The supernatant was discarded and the pellet was then resuspended with a syringe and needle in 1 ml of dissociation buffer (100 mM Tris [pH 9.0], 0.5 M NaCl, 100 mM urea, 10 mM EDTA, 5 mM DTT) and frozen overnight at −20° C. The next day, the solubilized protein was centrifuged at 13,300×g for 10 min and 500 µl of the supernatant was loaded onto two 5-25% (wt/vol) sucrose gradient made in dissociation buffer lacking protease inhibitors and spun at 274,000×g in a SW41Ti rotor (Beckman) for 16 h at 4° C. After centrifugation, the coat protein was harvested by fractionation on an ISCO gradient fractionator at 0.75 ml/min and 0.5 min/fraction. Fractions containing coat protein (typically fractions 6-12) were pooled and dialyzed against 100 mM Tris [pH 7.0], 500 mM NaCl, 10 mM EDTA overnight at 4° C. Samples were then concentrated (Amicon), aliquoted and stored at −80° C.

A different method was developed to purify soluble coat protein from Ac_416-787 infected cells. Unlike Ac_1-787 and Ac_1-415, recombinant protein from Ac_416-787 cells was soluble and could not be purified as above. To this end, frozen pellets of Ac_416-787 infected cells were resuspended in 2 volumes of TNE buffer and lysed by 3 cycles of freeze/thaw. Lysates were centrifuged for 10 min at 13,300×g, and the supernatant was collected. Aliquots of the supernatant were run on a 12% SDS-PAGE gel and the band corresponding to the recombinant protein was excised and eluted from the gel into TNE buffer. The protein was then stored at 4° C.

Example 5

HAstV-1 Coat Protein Displays Potent Complement Activity

Figure 2:
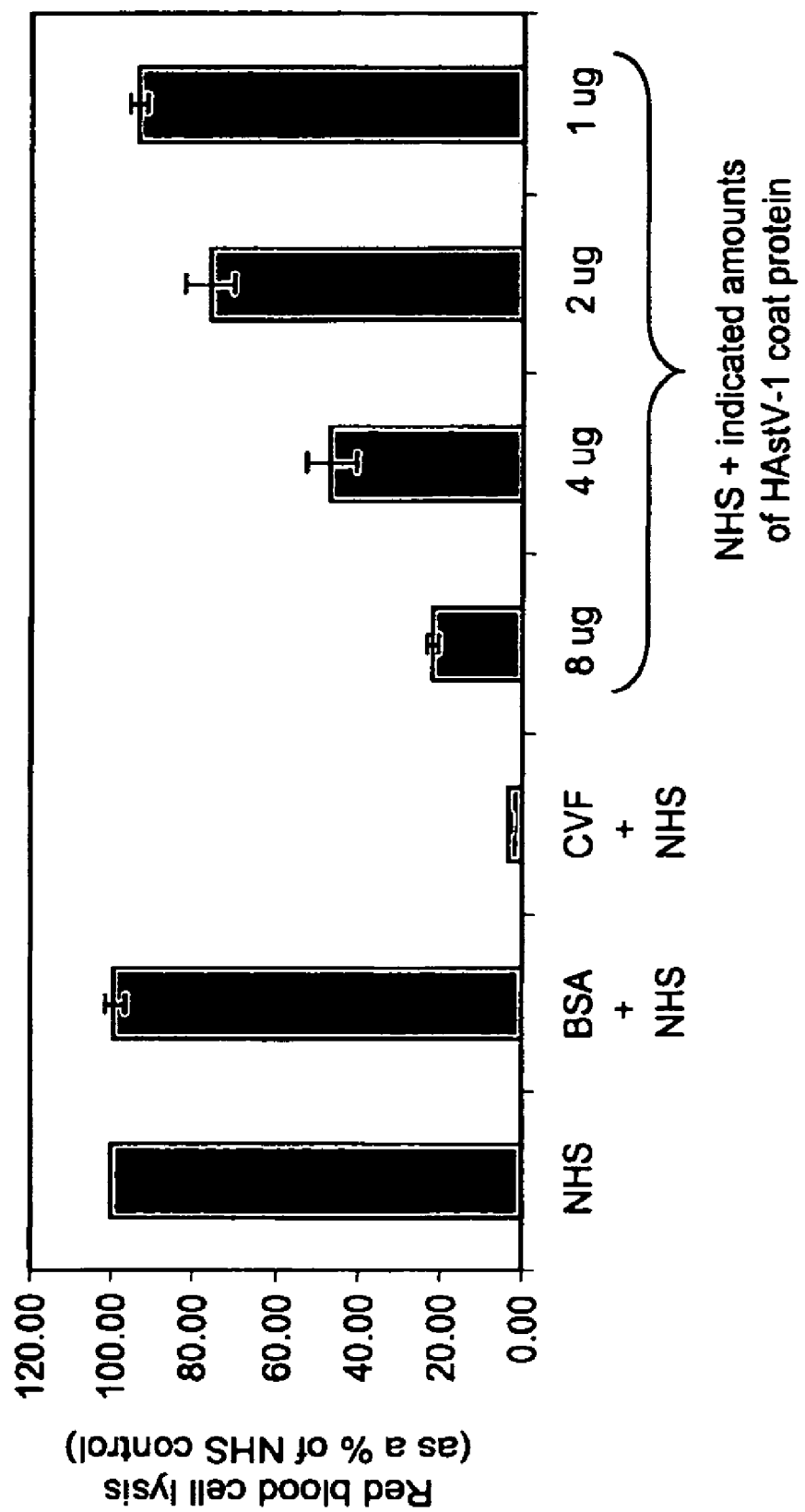
FIG. 2 is a graph depicting the results of the RBC assay on HAstV-1 coat protein. (n=3).
Figure 7:
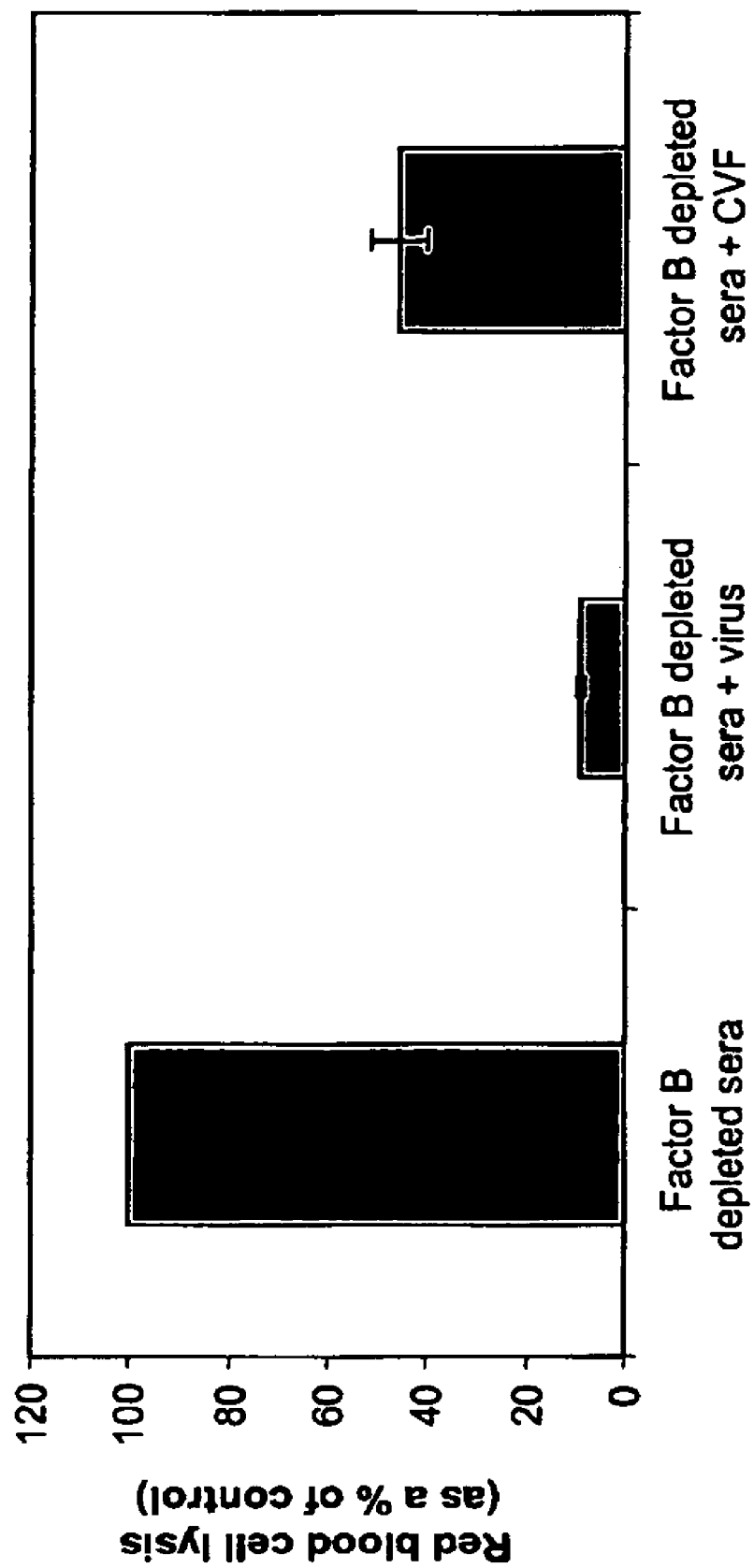
FIG. 7 is a graph depicting the results of the RBC assay used to test inhibition of the classical complement activation pathway by HAstV-1 virions and CVF. (n=3).
Figure 8:
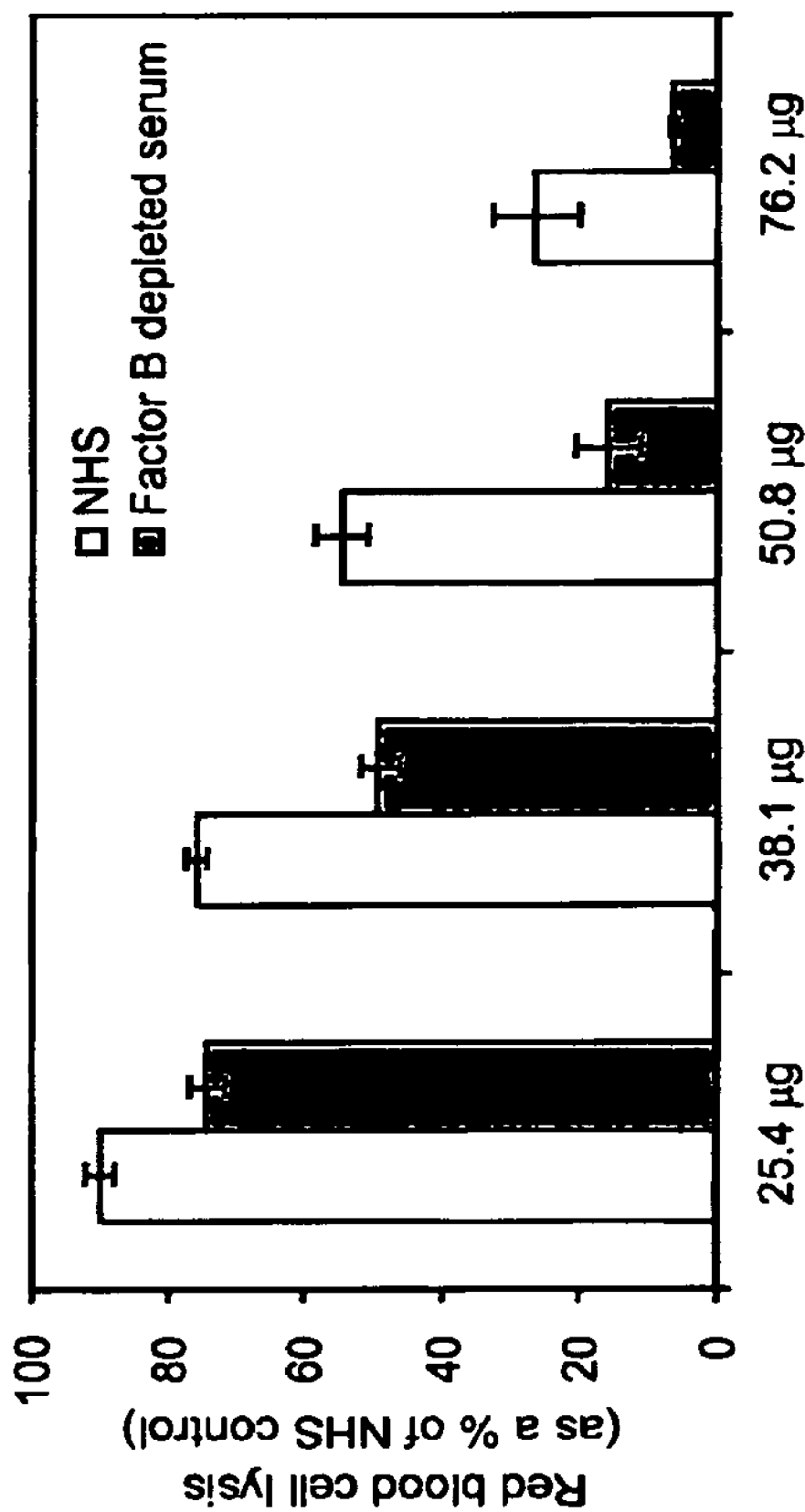
FIG. 8 is a graph depicting the results of the RBC assay used to test inhibition of the classical complement activation pathway by HAstV-1 coat protein compared to NHS (n=3).

The initial experiment that demonstrated coat protein activity on complement is shown in FIG. 2. In this assay, red blood cells (RBCs) are sensitized with antibody and incubated with normal human serum (NHS) causing lysis by complement activation (FIG. 2, NHS column). BSA (bovine serum albumin) is a negative control protein without complement effects and shows an equivalent amount of RBC lysis compared to NHS alone (FIG. 2, BSA+NHS column). Cobra venom factor (CVF) is a powerful activator of complement that causes depletion of complement components, thus inhibiting lysis of the RBCs; here CVF is used as a positive control (FIG. 2, CVF+NHS column). When increasing amounts of HAstV-1 coat protein was added to NHS, a dose response in RBC lysis was demonstrated indicating decreased complement activity. 1 ug of coat protein had a negligible effect whereas 8 ug exhibited >75% decreased RBC lysis by NHS (FIG. 2, last 4 columns on the right of graph). The fact that the coat protein inhibited RBC lysis to a similar degree as CVF is striking given that CVF is considered the most potent complement-depleting compound found in nature. Similar results are shown in FIG. 10, which illustrates an independent set of experiments (mean values for each are presented, n=4) using modified amounts of HAstV-1 coat protein from 12.2 μg to 19.4 μg added to NHS in the experimental samples. BSA and CVF controls, likewise, gave virtually identical results to those in FIG. 2.

Example 6

HAstV-1 Virions also Display Potent Complement Activity

While the HAstV-1 coat protein had complement activity, additional experiments were conducted to determine whether authentic, infectious HAstV-1 virions also strongly affected complement activity. To this end, varying amounts of virus in cell culture medium were added to NHS (FIG. 3). As expected, NHS alone completely lysed the RBCs, whereas CVF blocked lysis strongly. As more virus was added to NHS, a dose response was seen with 70 ul of the virus inhibiting lysis to the same extent as CVF. At 85 and 100 ul of virus, inhibition of RBC lysis surpassed that of CVF. As a control, NHS was incubated with equivalent amounts of uninfected tissue culture medium to show that this activity was virus specific (FIG. 4). Thus, both coat protein and whole virus demonstrated potent effects on the complement system. The data in FIG. 3 and FIG. 4 are presented side-by-side in FIG. 5, with viral genome copy number (×$10^8$) added to the axis.

Example 7

HAstV-1 Virions and CVF Display Similar Kinetics in the RBC Lysis Assay

To characterize the kinetics of activity of the astrovirus virions in the RBC lysis assay, a time course comparing HAstV-1 virions and CVF was conducted. HAstV-1 particles and CVF were incubated from 0 to 60 minutes in the presence of 2% NHS. At 0, 5, 15, 30 and 60 minutes, aliquots were removed and exposed to the sensitized RBCs (mean values are presented, n=3 to 5 for each sample). As shown in FIG. 6, both CVF and the virus showed similar kinetics in the inhibition of RBC lysis. The 60 minute time point suggests that the virus may have a stronger effect than CVF at this concentration as suggested above in FIG. 3 and FIG. 5. While this assay does not identify the complement factor(s) with which the coat protein/virus may interact, the data suggests that the coat protein/virus may activate and possibly deplete complement components in a similar fashion to CVF. Alternatively, the coat protein or virus may inhibit the formation of downstream complement complexes necessary for lysis of target cells.

Example 8

HAstV-1 Virions Affect the Classical and Alternative Pathways

Three pathways exist for the complement system, the classical (primarily activated by antigen:antibody interactions, mannan-binding lectin (binds specific polysaccharides on pathogen surfaces) and alternative (neither antibody nor lectin dependent) pathways (FIG. 1). As depicted in FIG. 7, the astrovirus virions specifically interact with the classical pathway leading to diminished activity as measured using Factor B depleted sera in the RBC lysis assay. Factor B is essential for alternative pathway activation allowing specific testing of classical pathway activation (FIG. 7, factor B depleted sera column). As with CVF, astrovirus particles inhibited RBC lysis in the absence of factor B indicating that this virus specifically blocks or depletes the classical pathway (FIG. 7). Similar results were obtained with HAstV-1 coat protein as illustrated in FIG. 8 (mean values presented, n=4). Taken together, these results indicate that HAstV-1 coat protein suppresses serum complement more effectively using factor B-depleted serum versus NHS, suggesting that HAstV-1 coat protein acts more strongly on the classical pathway than the alternative pathway. It is possible that the lectin pathway may also activate under these conditions.

Figure 9:
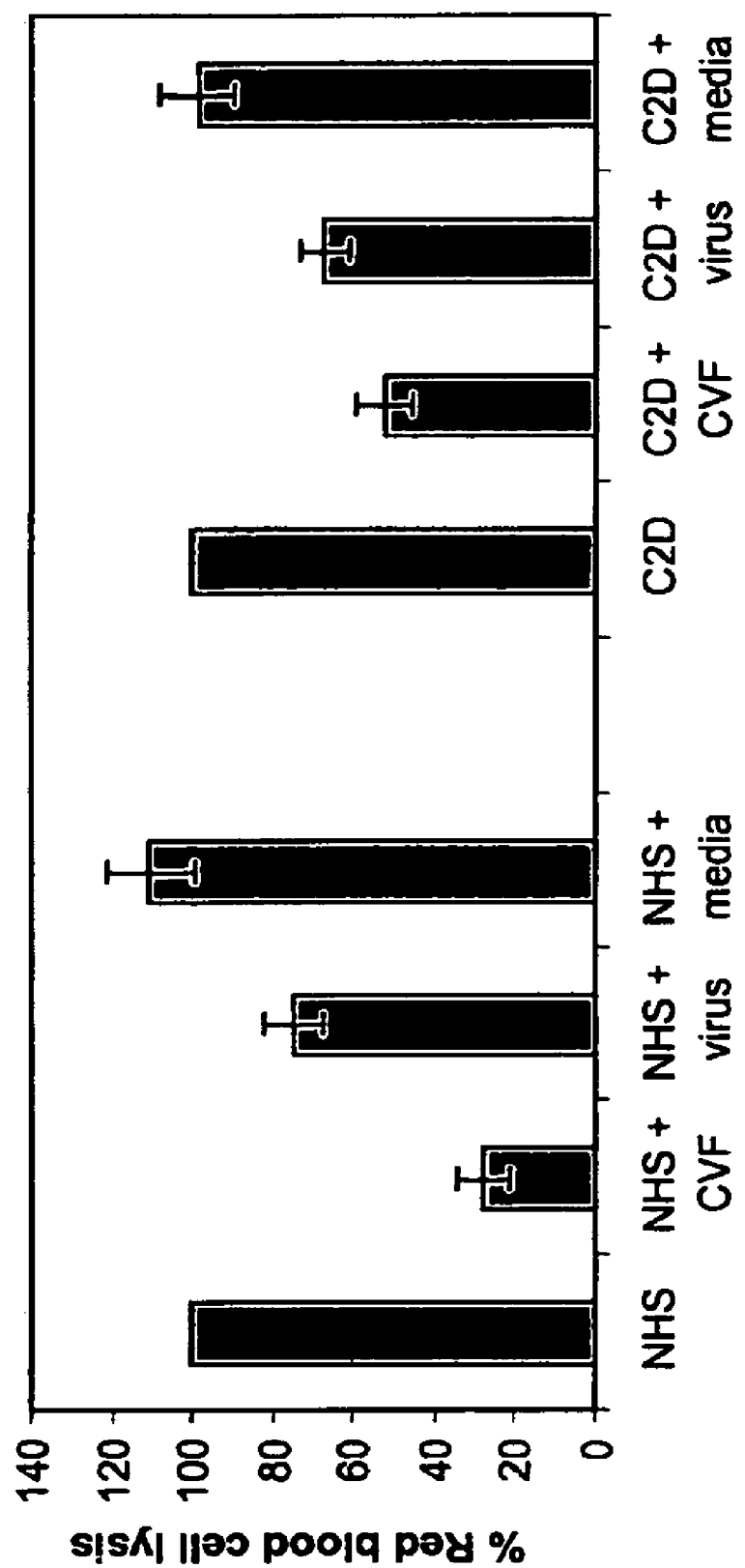
FIG. 9 is a graph depicting the results of the RBC assay used to test inhibition of the alternative complement activation pathway by HAstV-1 virions, uninfected cell culture medium and CVF. (n=3 to 5).
Figure 10:
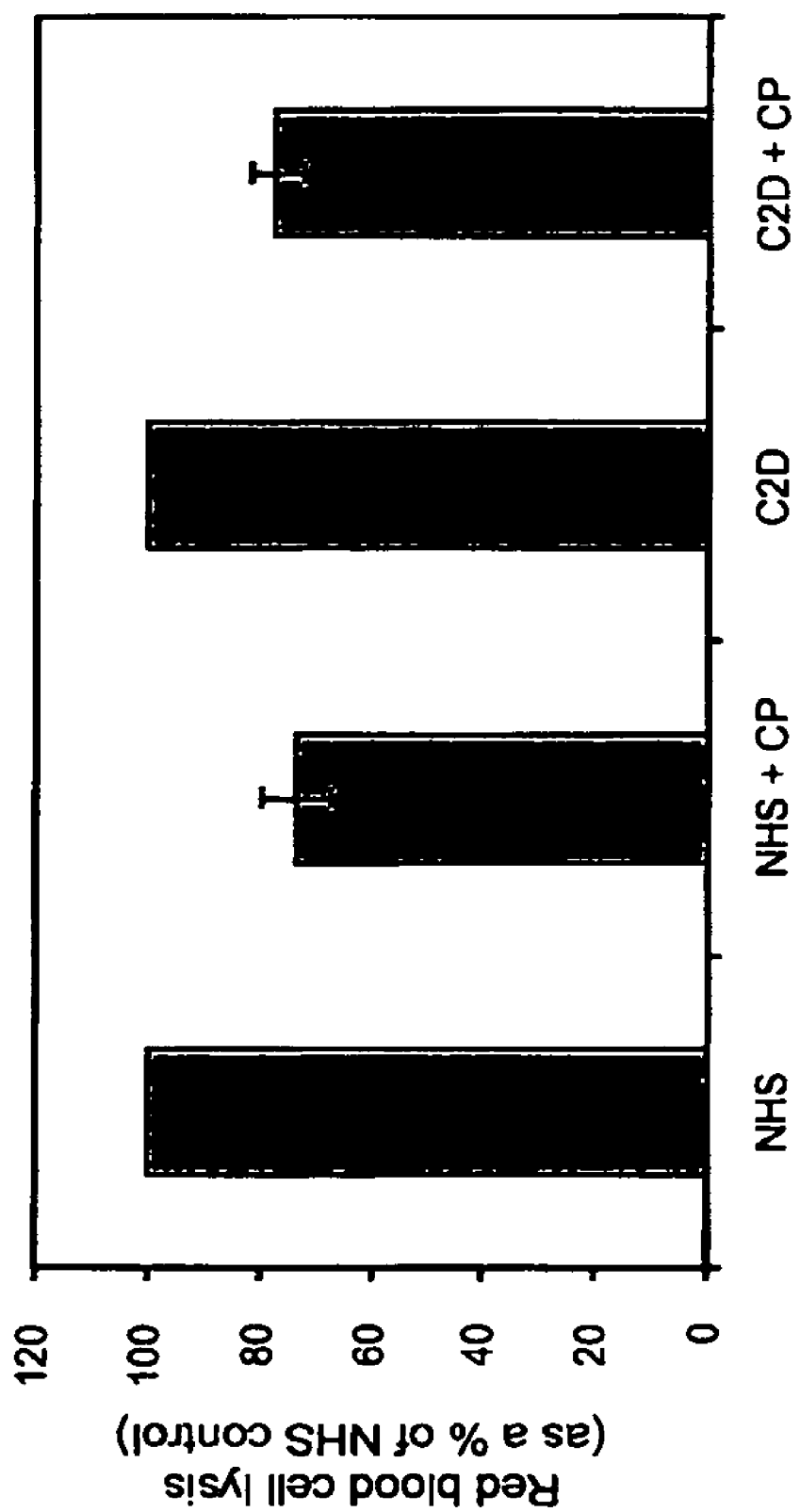
FIG. 10 is a graph depicting the results of the RBC assay used to test inhibition of the alternative complement activation pathway by HAstV-1 virions (n=3).

While HAstV-1 coat protein has dramatic ramifications for the classical pathway, HAstV-1 virions affect the alternative pathway to a lesser extent. As demonstrated in FIG. 9, in an assay to test for alternative pathway activation, NHS lyses rabbit RBCs as expected (NHS column). When CVF is added to NHS, lysis is significantly diminished (NHS+CVF column). In the presence of virus, lysis of cells is modestly affected (NHS+virus column). As a negative control, NHS in the presence of cell culture medium did not affect lysis as expected (NHS+media column). While this assay is set up to detect alternative pathway activation (i.e., the RBCs are not sensitized with antibody), the presence of astrovirus antibodies in NHS could potentially activate the classical pathway. To confirm that these findings were specific to the alternative pathway, C2 depleted serum (C2D) was utilized in the place of NHS (FIG. 9). By depleting NHS of C2 in this assay, the classical pathway and lectin pathways are blocked and any RBC lysis is due exclusively to alternative pathway activity. As expected, C2D in the absence or presence of cell culture medium lysed RBCs (C2D and C2D+media column). Both CVF and virus showed similar levels of inhibition of RBC lysis in this assay. These results demonstrate that HAstV-1 virions inhibit the alternative pathway to a lesser extent then the classical pathway and it is possible that the viral coat protein functions to block both pathways by completely different mechanisms. To further test for alternative pathway utilization, C2D sera was incubated with rabbit RBCs alone in Mg-EGTA-GVBS buffer or with 89 μg of purified HAstV-1 coat protein (n=3 for each). The results, depicted in FIG. 10, demonstrate that while HAstV-1 coat protein does in fact inhibit the alternative complement pathway as with virus (FIG. 9), the effect is minimal in comparison to the inhibitory effect on the classical pathway as illustrated above in FIG. 7 and FIG. 8. Again, the data demonstrates that while some alternative pathway inhibition is observable, the effect of astrovirus virions and coat protein is more significantly inhibitory of the classical pathway than the alternative pathway.

Example 9

Overlay Blot Assay

To ascertain whether HAstV-1 coat protein binds to specific complement factors, we utilized a modified virus overlay protein binding assay (VOPBA) approach (Borrow and Oldstone, 1992). To this end, 1 or 3 μg of purified complement factors C1, C1q, C1r, C1s, C2, C3 and C4 (Comptech) were mixed with 1×PBS and an equal volume of 2×SDS sample buffer lacking reducing agents and loaded onto a 7.5% SDS-PAGE gel. Following electrophoresis at 150V for 1 h, proteins were transferred to nitrocellulose and blocked in 5% NFDM-PBS-0.001% Tween-20 for 1 h at room temperature. Purified WT coat protein was then added (~10-20 μg) to the blot and allowed to incubate for 1 h, after which the blot was washed extensively with PBS-0.001% Tween-20. The rest of the procedure was carried out as for a standard immunoblot as described above.

Figure 11:
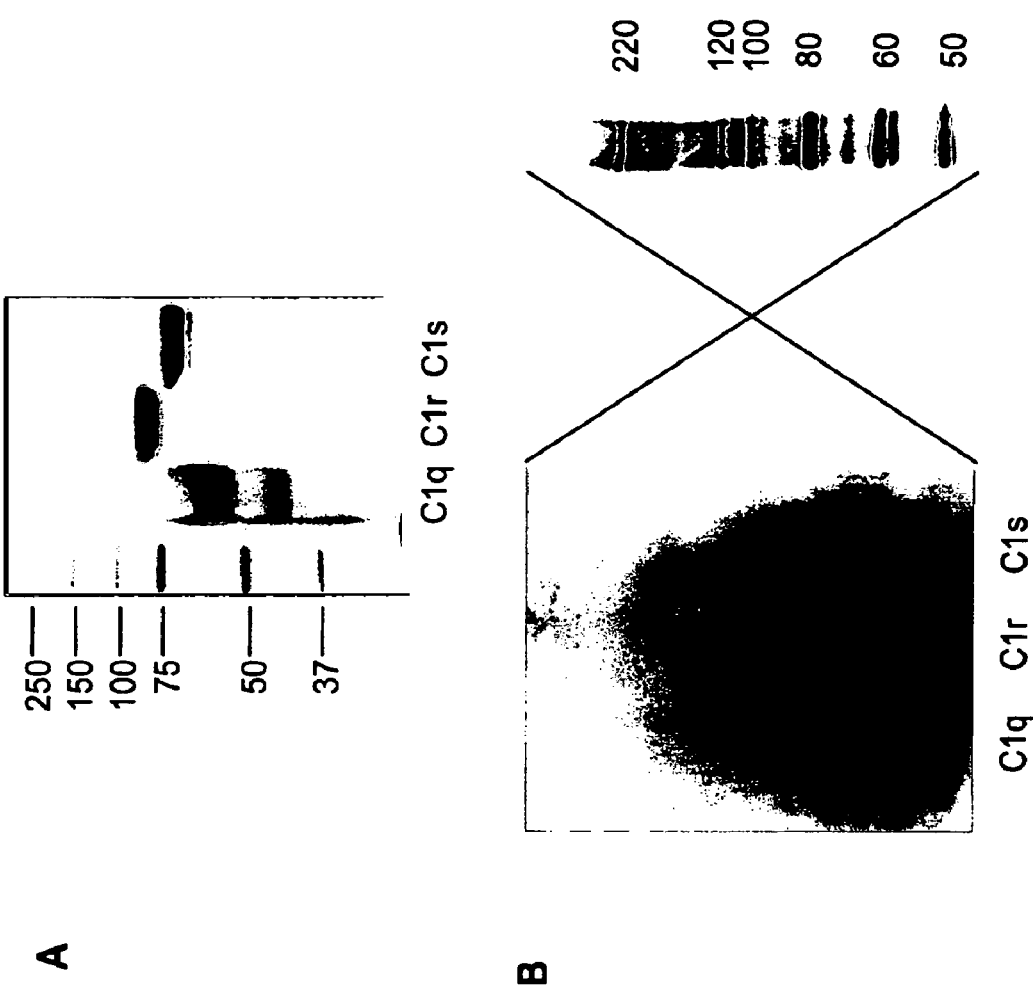
FIG. 11A is an image of the 7.5% SDS-PAGE gel loaded with C1q, C1r, and C1s, and run in non-reducing conditions with Coomassie blue staining.
FIG. 11B is an image of a nitrocellulose blot transferred from a 7.5% SDS-PAGE gel loaded with C1q, C1r, and C1s, run in non-reducing conditions and probed with wildtype HAstV-1 coat protein.

An approximately 59 kDa band was detected in the C1 preparation. It is contemplated that other preparations of complement proteins may interact with wildtype astrovirus coat protein or derivatives under conditions differing from those exemplified here. In order to further investigate the binding of HAstV-1 coat protein to complement protein C1, the blotting protocol was repeated with purified C1 complex components C1q, C1r, and C1s. Total protein staining with Coomassie blue is depicted in FIG. 11A, while results for the blotting experiment are depicted in FIG. 11B. The result suggests that HAstV-1 wildtype coat protein interacts with a C1q band in the 50-60 kDa range, and the C1r component binds just above 80 kDa. However, subsequent experiments demonstrated that the 80 kDa band was an artifact caused by the primary antibody to HAstV-1 virions non-specifically interacting with the C1r homodimer in the absence of the coat protein probe. As the data in FIG. 12C indicates (see below), the coat protein binds specifically to C1q.

Figure 3:
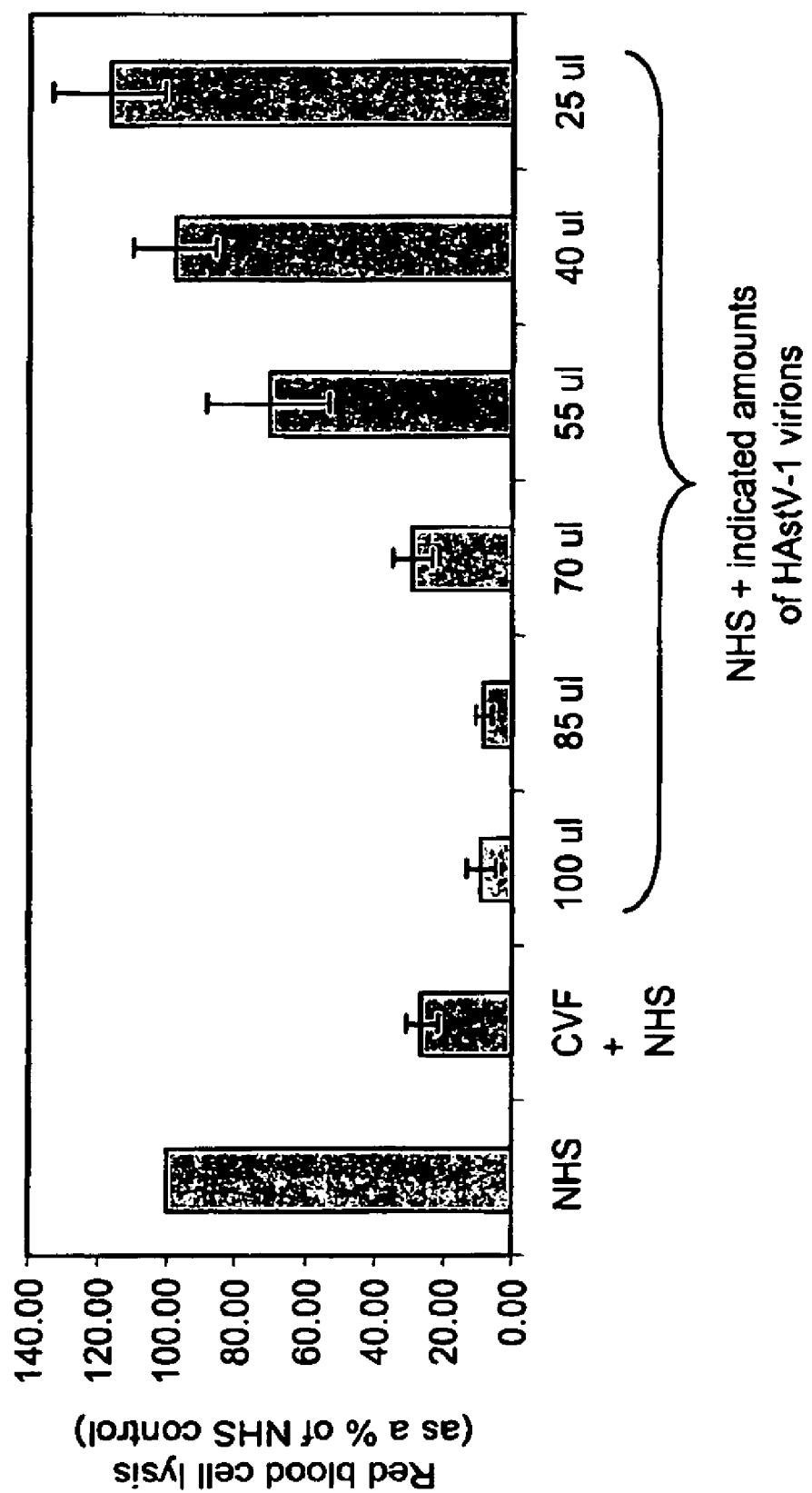
FIG. 3 is a graph depicting the results of the RBC assay on HAstV-1 virions. (n=5).
Figure 4:
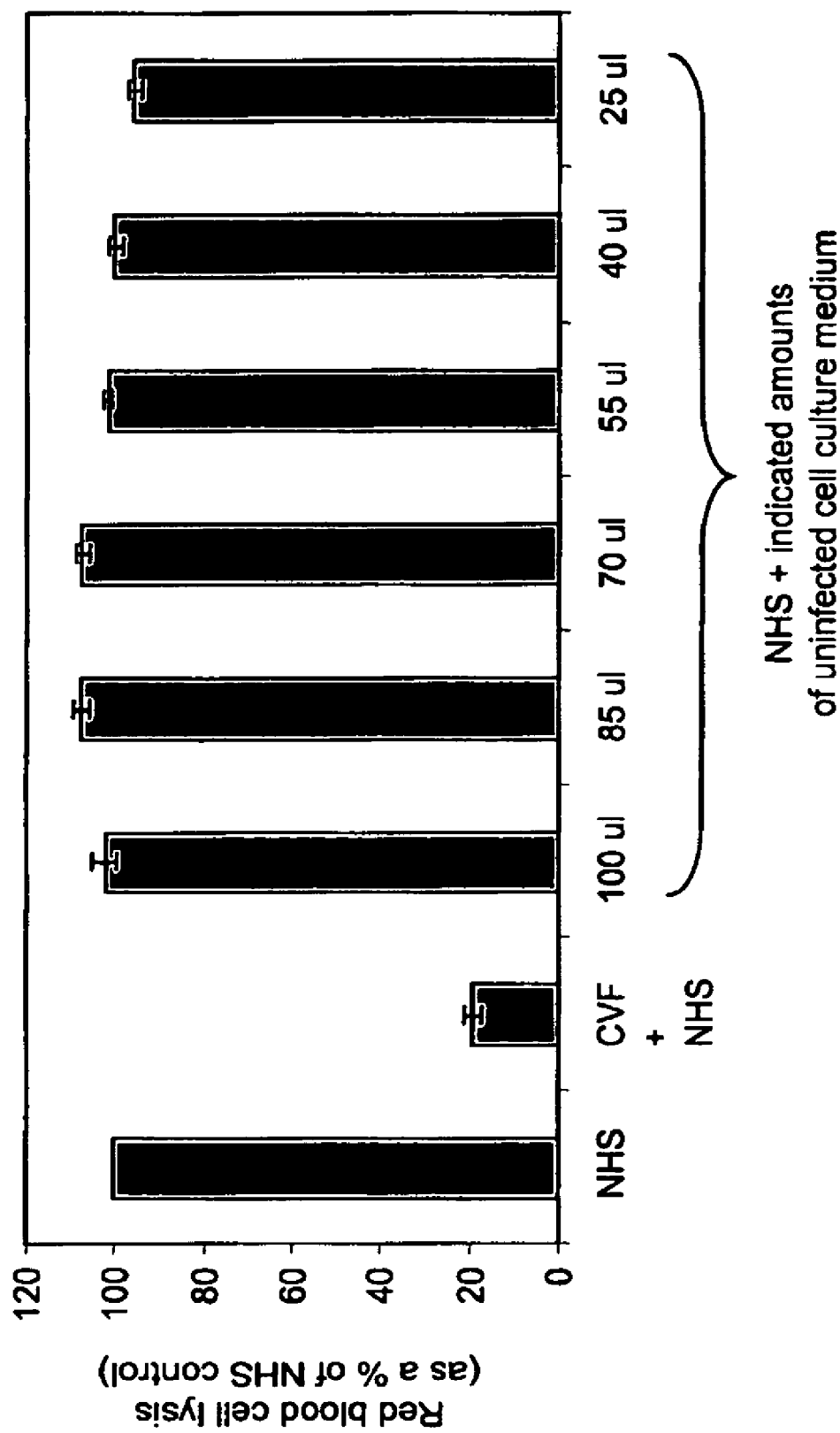
FIG. 4 is a graph depicting the results of the RBC assay on uninfected cell culture medium. (n=3).
Figure 5:
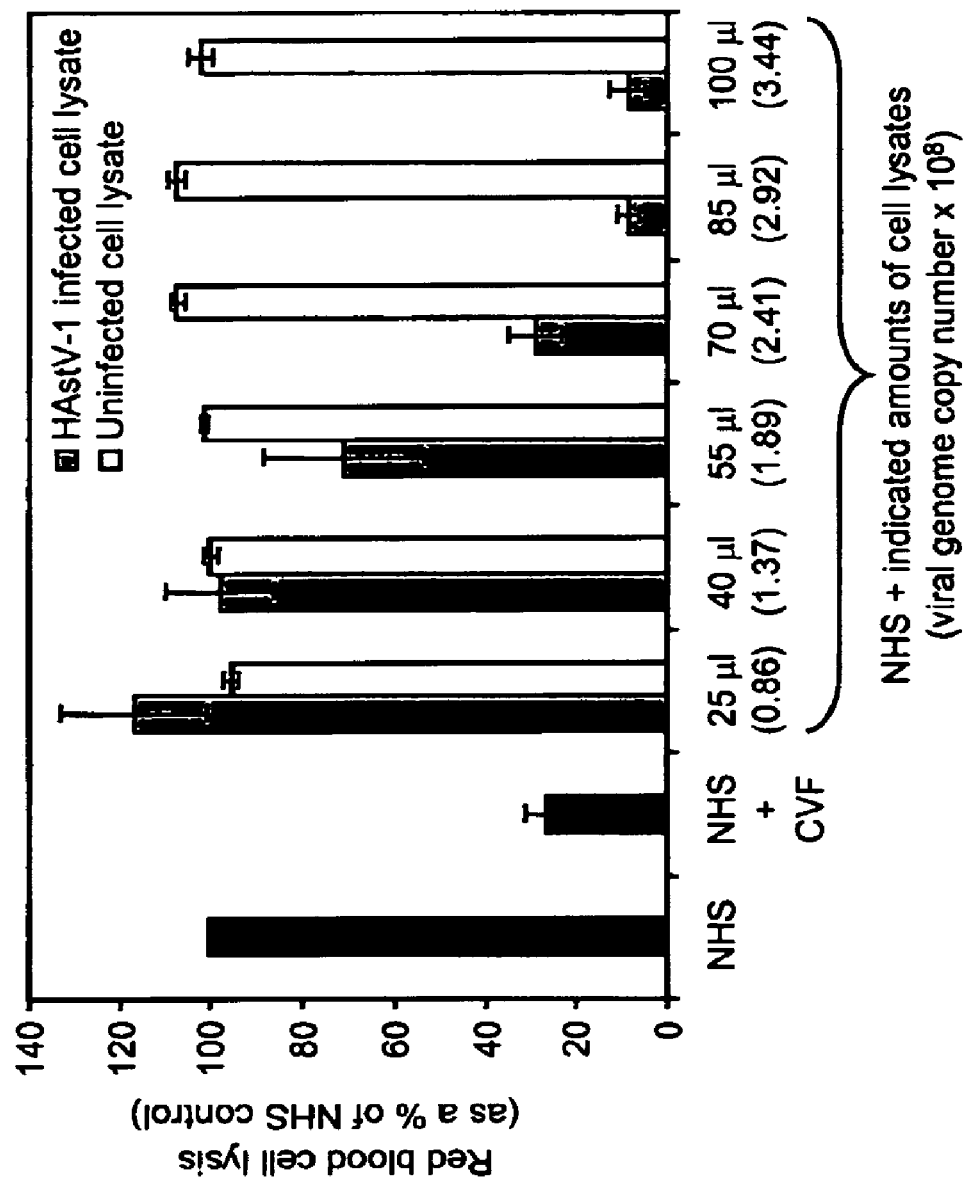
FIG. 5 is a graph depicting the suppressive activity of HAstV-1 virions on RBC lysis.
Figure 6:
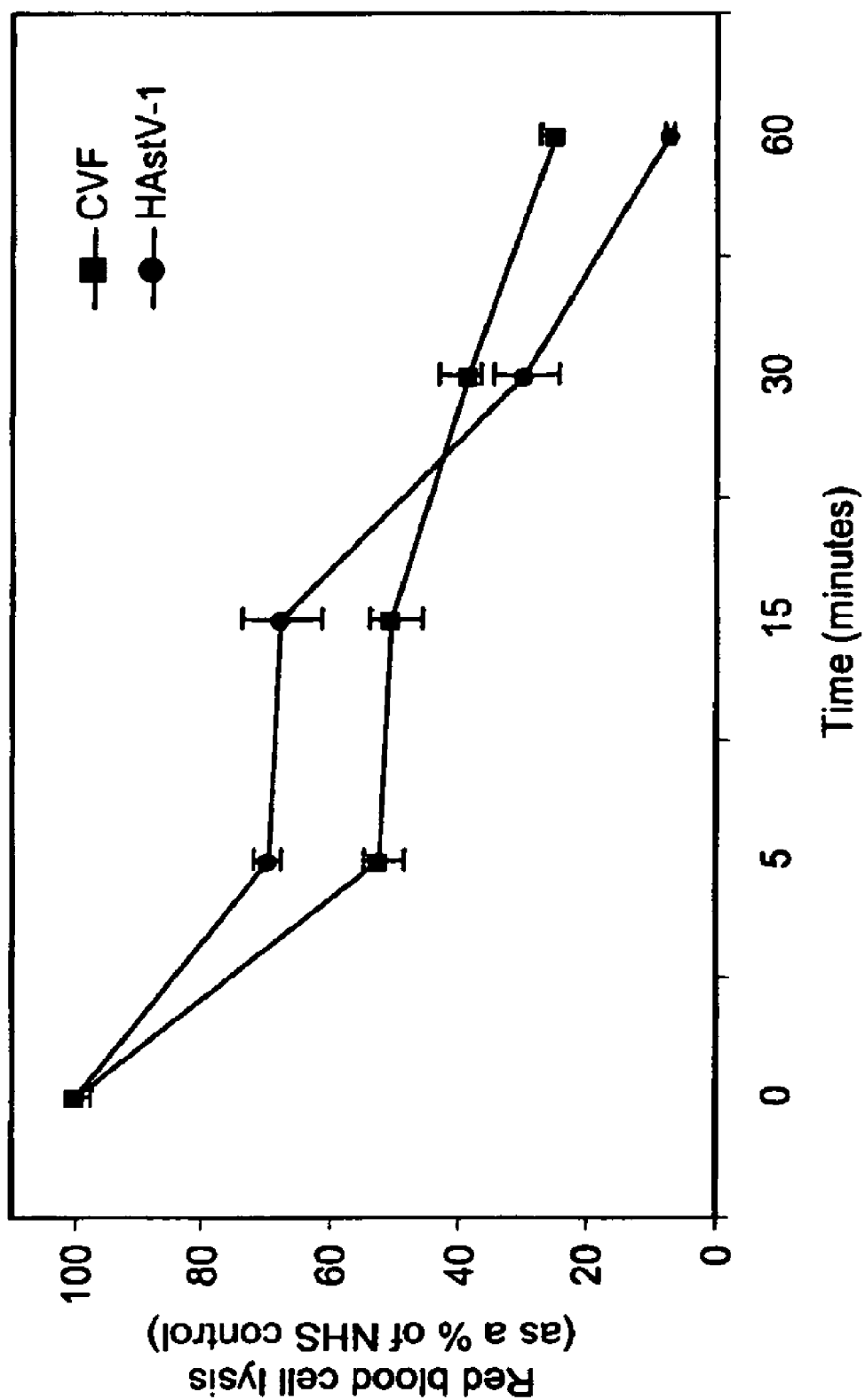
FIG. 6 is a graph illustrating the comparative time course of RBC lysis of CVF and HAstV-1. (n=3 to 5).
Figure 12:
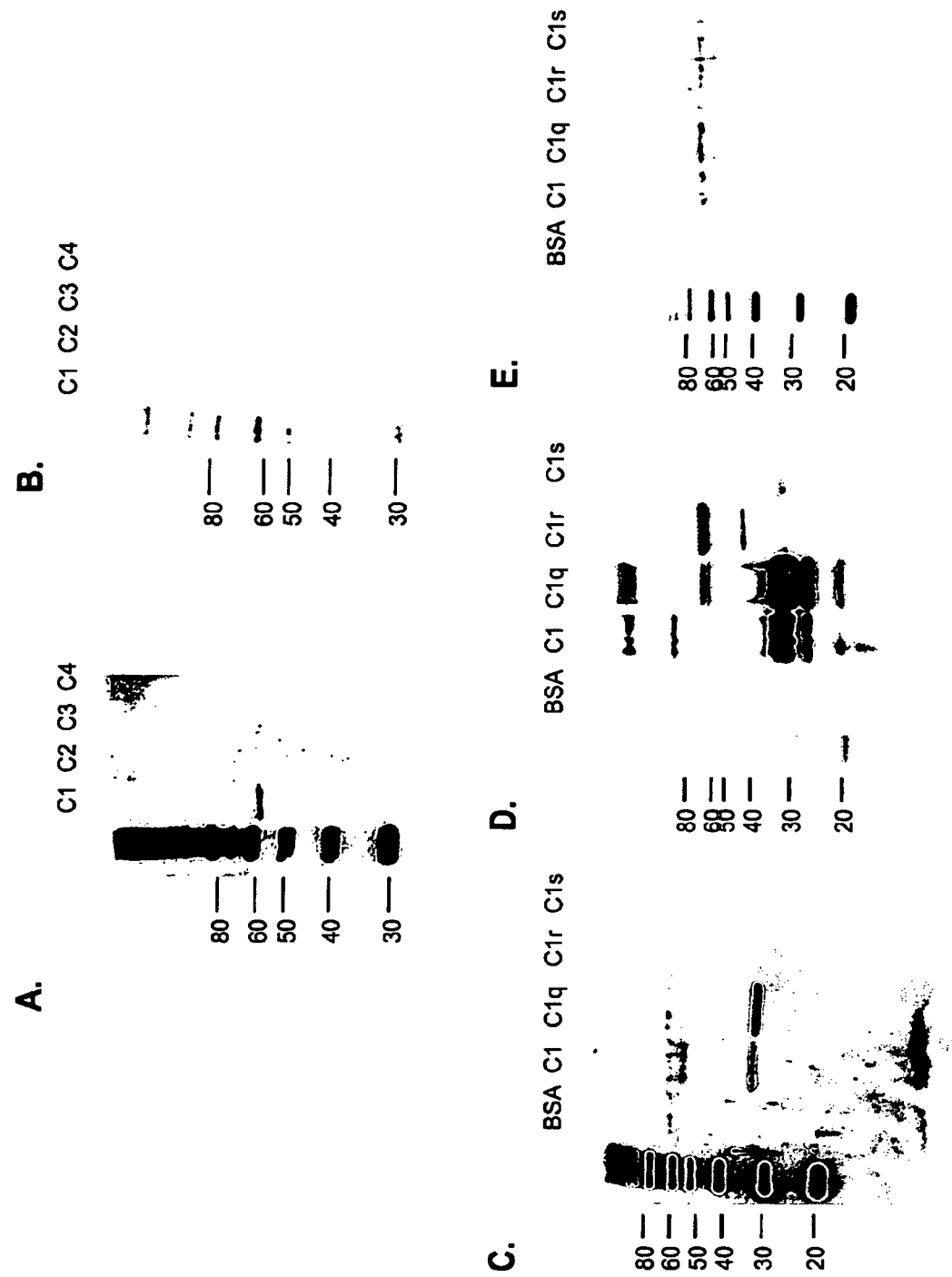
FIG. 12A-E are collectively a series of illustrative panels indicating that HAstV-1 coat protein binds complement protein C1q.

Further experiments confirmed the initial finding that HAstV-1 coat protein binds C1q in an overlay blot assay. In FIG. 12A, purified complement factors C1, C2, C3 and C4 (Comptech) were mixed with 1×PBS and an equal volume of 2×SDS sample buffer lacking reducing agents and loaded onto a 7.5% SDS-PAGE gel without boiling the samples. Following electrophoresis at 150V for 1 h, proteins were transferred to nitrocellulose and blocked in 5% NFDM-PBS-0.01% Tween-20 for 1 h at room temperature. Purified coat protein was then added (~10 μg) to the blot and allowed to incubate for 1 h, after which the blot was washed extensively with PBS-0.001% Tween-20. The rest of the procedure was carried out as for a standard immunoblot using primary antibody to HAstV-1 virions and an appropriate HRP-conjugated secondary antibody. In FIG. 12B, the same experiment was performed as in FIG. 12A above, except no coat protein probe was utilized. In FIG. 12C, 3 μg of BSA, C1, C1q, C1r and C1s were mixed with 1×PBS and an equal volume of 2×SDS sample buffer containing reducing agents, boiled and loaded onto a 12% SDS-PAGE gel. The overlay blotting was then carried out as in FIG. 12A. In FIG. 12D, the overlay blot in FIG. 12C was stripped with Restore Western blot stripping buffer (Pierce) according to the manufacturer's guidelines and probed with polyclonal antibodies to C1q, C1r and C1s (Santa Cruz) followed by the appropriate HRP-conjugated secondary antibody. FIG. 12E represents a duplicate blot as in FIG. 12C except no coat protein probe was utilized.

The above experiments demonstrate that the coat protein binds to something in C1 that migrates at about 59 kDa. Because these samples were not boiled or reduced and the C1 preparation purchased from Comptech is contaminated with other serum proteins, further experiments were necessary to rule out the possibility that the coat protein was binding to something other than a C1 constituent, e.g., C1q, C1r, or C1s. The three highly purified C1 components, boiled and reduced, were run on a gel and the experiment was repeated. This time, an approximately 34-kDa band was detected in both the C1 and C1q lane. A 34-kDa band is consistent with the C chain of the C1q protein. C1q, when fully oxidized and reduced, breaks into three separate chains: chain A runs at 27.5 kDa, chain B runs at 31.6 kDa, and chain C runs at 34 kDa (Cooper, N. R., 1985. *Adv. Immunol.* 37, 151-216). The overlay blot was stripped and probed with antibody to C1q, C1r, and C1s. When the previous blot was aligned to the re-probed blot, the band in the overlay corresponded to the C1q C chain. The 59 kDa band seen in FIG. 12A probably represents one of the doublet bands seen in the C1q lane in FIG. 12D. This doublet is most likely a C—C chain and A-B chain dimer, which has been reported (Cooper, N. R., 1985. *Adv. Immunol.* 37, 151-216) to run at 54 kDa and 69 kDa, respectively. The sum of these experiments is that astrovirus coat protein interacts with a C1q chain in this in vitro binding assay.

Example 10

Other HAstV Serotypes Suppress Hemolytic Complement Activity

To determine whether HAstV serotypes other than the type 1 exhibit the same effects on complement activity, equivalent amounts cell lysates infected with serotypes 1-4 ($2.92 \times 10^8$ genome copies each) were analyzed in the RBC lysis assay with all four serotypes demonstrating comparable levels of hemolysis inhibition (Table 2). These findings suggest that the complement suppressing effect reported here is a conserved property of the HAstVs.

TABLE 2

RBC lysis assay on HAstV serotypes 1-4

| HAstV serotype [a] | Inhibition of hemolysis (%) [b] | SE |
|---|---|---|
| 1 | 86.3 | 2.38 |
| 2 | 84.3 | 3.14 |
| 3 | 86.3 | 3.14 |
| 4 | 87.0 | 0.47 |

[a] $2.92 \times 10^8$ genome copies from infected cell lysates were utilized for each serotype tested.
[b] n = 3

Example 11

Analysis of Recombinant Coat Protein Oligomerization

Figure 13:
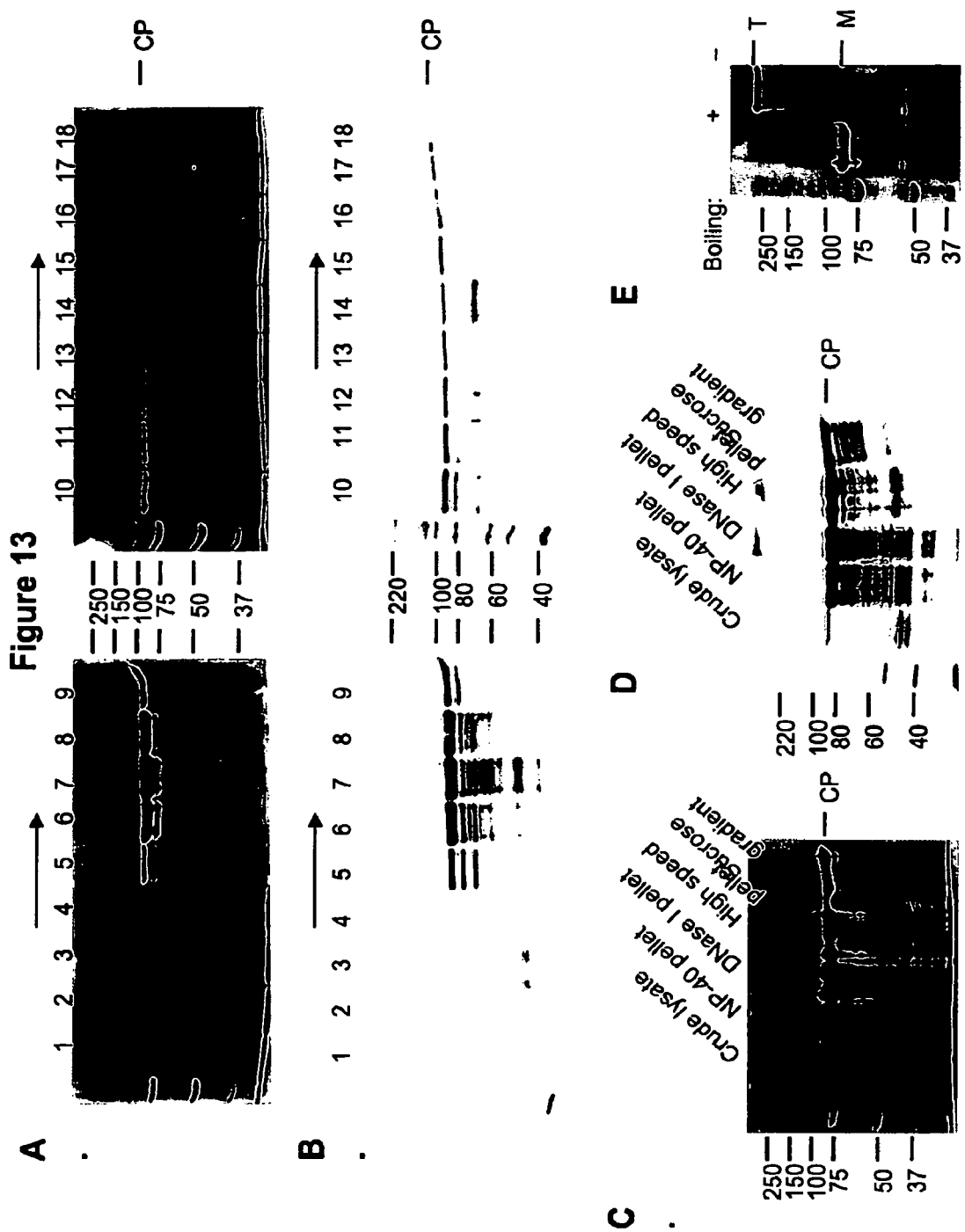
FIG. 13A-E are images of SDS-PAGE gels (A, C, and E) and immunoblots (B and D) from experiments analyzing HAstV-1 coat protein purification procedure and demonstrating the spontaneous oligomerization by the coat protein.

SDS-PAGE and immunoblot analysis of the HAstV-1 coat protein purification procedure and demonstration of spontaneous oligomerization by the coat protein. As illustrated in FIG. 13A, aliquots of the first 18 fractions from the sucrose gradient ultracentrifugation step of the purification procedure were analyzed on 7.5% SDS-PAGE gels. The gels were then stained with Coomassie blue. Fraction numbers are located at the top of the gels and the arrows indicate the direction of sedimentation from the top to bottom of the gradient. The migration of the 87 kDa coat protein (CP) is indicated. In FIG. 13B, immunoblot analysis of the same gradient fractions utilizing an antibody to HAstV-1 virions. FIG. 13C illustrates a 7.5% SDS-PAGE analysis of the coat protein containing fraction at each stage of the purification procedure as analyzed by Coomassie blue staining and FIG. 13D represents the immunoblot of the same gel. In FIG. 13E, aliquots of sucrose-purified coat protein were either boiled or not boiled in the presence of 2-mercaptoethanol and run on a 7.5% SDS-PAGE gel. The gel was then stained with Coomassie blue. The boiled protein migrates at approximately 87 kDa, the expected mass of the uncleaved coat protein precursor (monomer, M) whereas the unboiled sample migrates above 250 kDa possibly representing a trimer (T) which would be postulated to run at 261 kDa. For all gels and blots, the molecular weight markers (in kDa) are indicated.

Example 12

Figure 14:
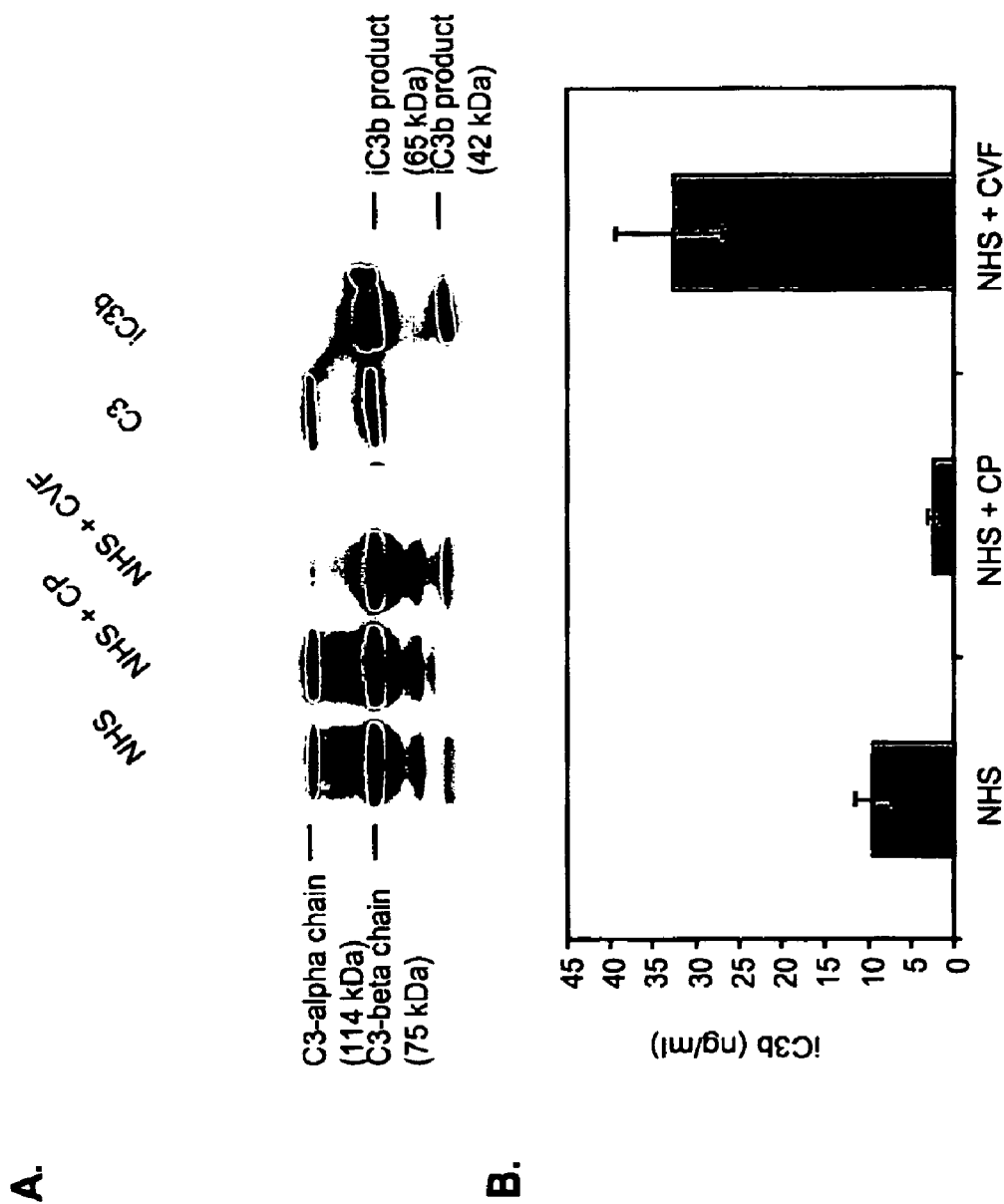
FIG. 14A is an image of an immunoblot showing a comparison of iC3b production in NHS alone, NHS plus HAstV-1 coat protein or NHS plus CVF.
FIG. 14B is a graph depicting the results of an ELISA quantifying the amount of iC3b (in ng/mL) produced in NHS alone, NHS plus HAstV-1 coat protein or NHS plus CVF.
FIG. 14C is a graph depicting the results of an ELISA quantifying the amount of SC5b-9 (in ng/mL) produced in NHS alone, NHS plus HAstV-1 coat protein or NHS plus CVF.
Figure 14:
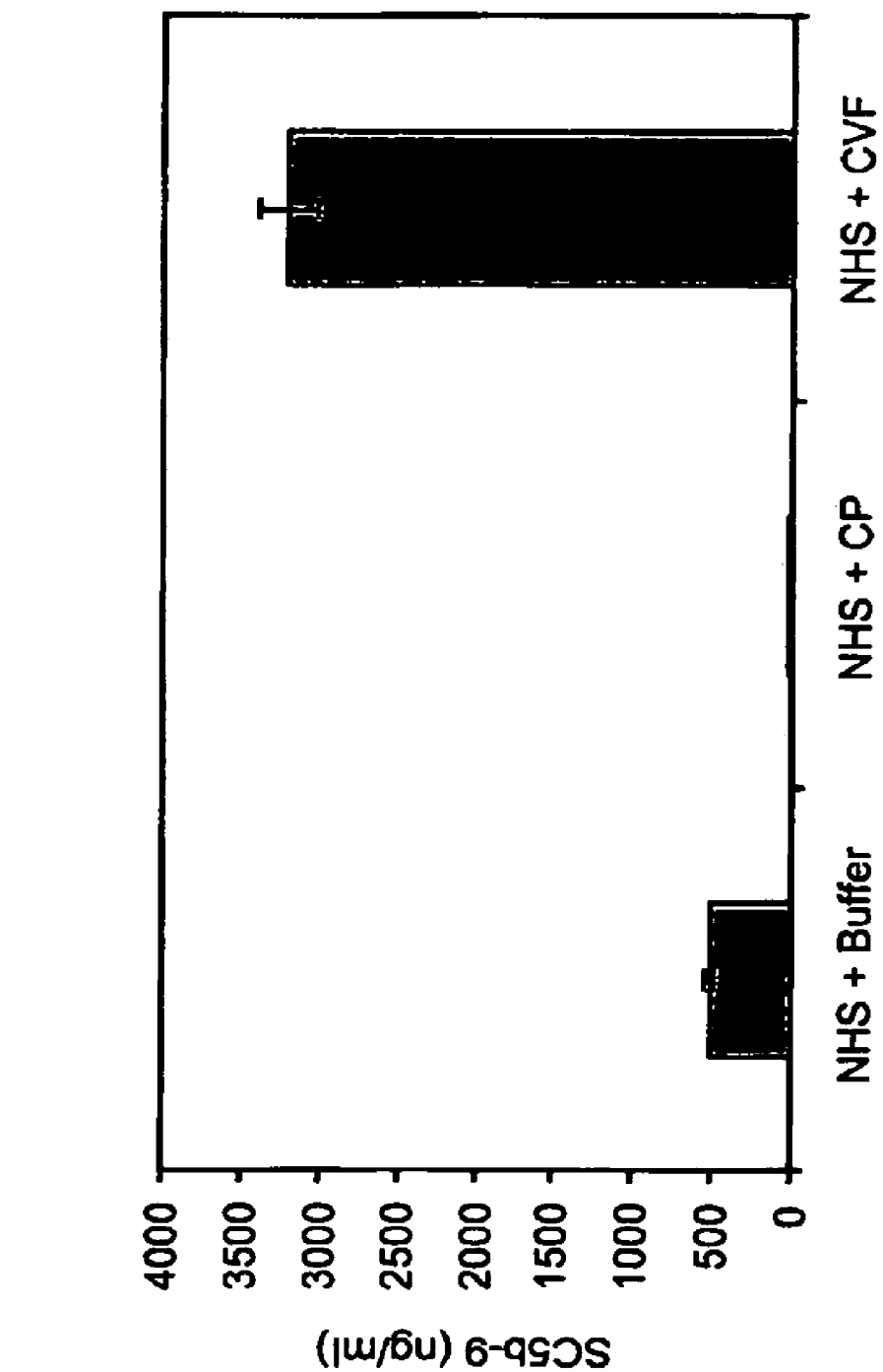

HAstV-1 Coat Protein Inhibits iC3b Formation and Activation of the Terminal Pathway Antibody sensitized sheep RBCs were incubated with NHS alone, with 1 µg CVF or with 76 µg of purified HAstV-1 coat protein (CP) for 3 hours at 37° C. As represented in FIG. 14A, aliquots of each reaction were boiled and reduced, run on a SDS-PAGE gel, transferred to nitrocellulose and probed with a polyclonal antibody to C3. Positive controls for C3 alpha (114 kDa) and beta (75 kDa) chain along with the two iC3b products (65 kDa and 42 kDa) are indicated. These results demonstrate that NHS in the presence of HAstV-1 coat protein does not generate significant amounts of iC3b. The presence of iC3b is an indication of C3 convertase formation, i.e. activation of either the classical, alternative or mannose-binding lectin pathways. In FIG. 14B, an iC3b ELISA was performed on the samples using a monoclonal antibody to iC3b. The absorbance of the supernatants was read in a spectrophotometer at 405 nm. A standard curve was utilized to determine the values of iC3b (ng/ml). Data are means of four independent experiments. Error bars denote standard errors of the means. These results further confirm that NHS in the presence of coat protein does not generate significant amounts of iC3b. The observation that even less iC3b is generated with the addition of coat protein than with the addition of NHS alone is remarkable as NHS normally produces iC3b spontaneously, a process known as "tickover." Aliquots of the same 3 samples were subject to a SC5b-9 ELISA using a monoclonal antibody to SC5b-9. The absorbance of the supernatants was read in a spectrophotometer at 405 nm. A standard curve was utilized to determine the values of SC5b-9 (ng/ml), as illustrated in FIG. 14C. Data are means of four independent experiments. Error bars denote standard errors of the means. The ELISA data in FIG. 14C demonstrates that the terminal complement complex (known alternatively as the membrane attack complex or "MAC") is completely inhibited from formation in the presence of astrovirus coat protein. These observations taken as a whole indicate that astrovirus coat protein inhibits the complement system, a distinct mechanism from complement depletion as mediated by CVF. The fact that coat protein can inhibit the system upstream of C3 is significant as this prevents the formation of the C3a and C5a anaphylatoxins as well as MAC formation. Prevention of those products of the complement cascade greatly enhance the therapeutic value of the coat proteins because they fail to activate the cascade, unlike CVF.

Example 13

Exogenous C1 Reverses the Inhibition of Hemolytic Activity and Deposition of C3 on Zymosan by HAstV-1

Figure 15:
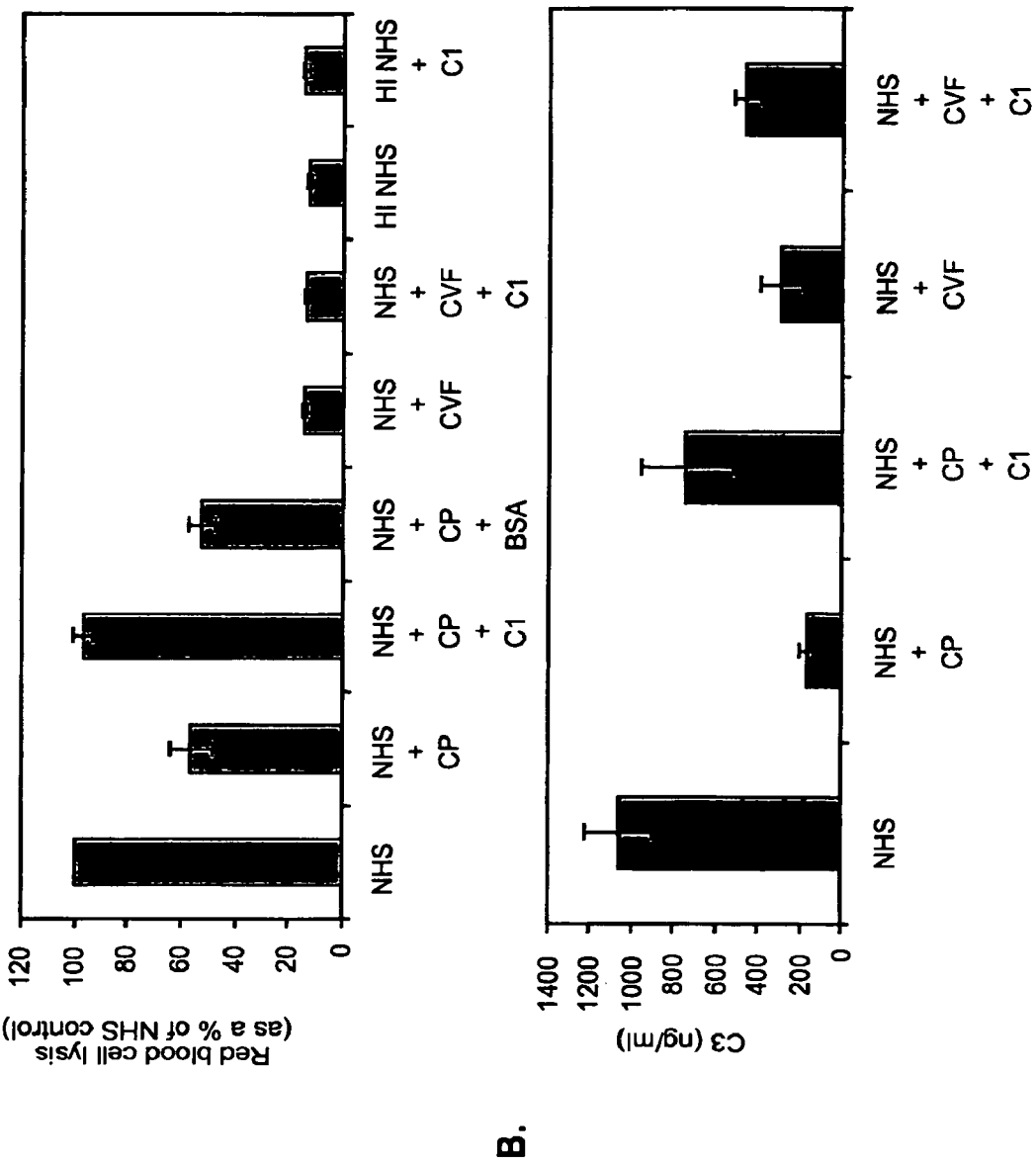
FIG. 15A is a graph depicting the reversal of HAstV-1 coat protein inhibition of complement lysis by the addition of exogenous C1 protein in an RBC lysis assay.
FIG. 15B is a graph depicting the results of an ELISA for quantifying C3 (in ng/mL) deposition on zymosan in samples with NHS alone, NHS plus HAstV-1 coat protein (with or without the addition of exogenous C1), or NHS plus CVF (with or without the addition of exogenous C1).

In order to further define the role of C1 in the inhibition of complement-mediated lysis by HAstV-1, HAstV-1 inhibition of hemolytic activity was tested for reversibility by the addition of exogenous C1. NHS was incubated with 47 µg coat protein (CP) or 1 µg CVF for 1 hour at 37° C. 47 µg of CP was used to achieve approximately 50% RBC lysis. After the incubation, 10 µl of C1 (~1 mg/ml) or 10 µl BSA (1 mg/ml)

was added back to the indicated samples as shown in FIG. 15A. Simultaneously, RBCs were added to all samples. Heme lysis was standardized to 100% for NHS alone. "HI-NHS" indicates the use heat inactivated NHS. Data from the RBC lysis assay are means of results from four independent experiments. Error bars denote standard errors of the means. In FIG. 15B, 20 μl of NHS was added to either (i) 50 μl GVBS-- buffer and incubated alone, (ii) with 67 μg (50 μl) coat protein, or with 1 μg CVF in 49 μl of GVBS++ buffer. All volumes were brought up to 1 ml using GVBS++ buffer and incubated for 1 hour at 37° C. After incubation, 15 μl C1 (~1 mg/ml) was added to the indicated samples and subsequently 25 μl zymosan was added to all samples. After a 10 minute incubation at 37° C., the samples were washed twice in GVBS++ buffer and treated with 30 μl of 25 mM methylamine for 1 hour in a 37° C. water bath before being spun down and the supernatant collected. A C3 ELISA was performed on the samples using a polyclonal antibody to C3. The absorbance of the supernatants was read in a spectrophotometer at 405 nm. A standard curve was utilized to determine the values of C3 (ng/ml). Data is presented as the mean values of four independent experiments. Error bars denote standard errors of the means.

In FIG. 15A, the amount of HAstV-1 coat protein was titered to an amount necessary to achieve 50% RBC lysis. When C1 protein was added back to the mixture, the hemolytic activity was completely restored. In contrast, restoration of hemolytic activity by adding back BSA, CVF, or heat-inactivated NHS does not occur. In FIG. 15B, the C1 add-back data presented in FIG. 15A was confirmed using a different approach. In this experiment, NHS is added to zymosan, which activates serum complement and leads to the deposition of C3 on the zymosan. Methylamine is then used to strip the C3 off the zymogen and the C3 levels are assayed by ELISA. In the presence of the coat protein, there is very little C3 deposition, as expected. When C1 is added back, more C3 is present, indicating that the effect of the coat protein is overcome. Adding C1 to CVF, conversely, has no significant effect. The sum of the experiments illustrated in FIGS. 15A and 15B indicate that HAstV-1 coat protein inhibits the classical pathway of complement activation through interaction with the C1 complex.

We claim:

1. A method for identifying an Astroviridae family coat protein or derivative thereof capable of regulating complement cascade protein activity comprising combining a purified coat protein or derivative thereof of an astrovirus with target cells and complement cascade proteins and measuring the lysis of said target cells by said complement cascade proteins.

2. The method of claim 1, wherein the coat protein or derivative is a viral-like particle.

3. The method of claim 1, wherein the coat protein or derivative is purified from wildtype virus.

4. The method of claim 1, wherein the coat protein or derivative is produced by recombinant technology.

5. The method of claim 4, wherein the coat protein or derivative is produced in a recombinant protein expression method from a group consisting of a baculovirus system, *E. coli* cells, and yeast cells.

6. The method of claim 1, wherein the target cells are red blood cells.

7. The method of claim 6, wherein the coat protein or derivative inhibits lysis of red blood cells in the presence of normal human serum.

8. The method of claim 1, wherein the regulation of complement cascade protein activity is measured as a time course comparing said coat protein or derivative with the ability of a known complement cascade-regulating compound to inhibit target cell lysis.

9. The method of claim 8, wherein the known complement cascade-regulating compound is cobra venom factor (CVF).

10. The method of claim 1, wherein the regulation of complement cascade protein activity by an Astroviridae family coat protein or derivative is inhibition of the classical complement cascade pathway.

11. The method of claim 10, wherein the inhibition of the classical complement cascade pathway is determined by adding the Astroviridae family coat protein or derivative to target cells and complement cascade proteins substantially depleted of complement Factor B.

12. The method of claim 1, wherein the regulation of complement cascade protein activity by an Astroviridae family coat protein or derivative is inhibition of the alternative complement cascade pathway.

13. The method of claim 12, wherein the inhibition of the alternative complement cascade pathway is determined by combining the Astroviridae family coat protein or derivative with target cells in the presence of complement cascade proteins substantially depleted of complement Factor B.

14. The method of claim 1, wherein the regulation of complement cascade protein activity by an Astroviridae family coat protein or derivative is inhibition of the lectin complement cascade pathway.

15. The method of claim 1, wherein the coat protein or derivative further inhibits activation of the terminal pathway of the complement cascade.

16. The method of claim 1, wherein the coat protein or derivative is further tested for binding to specific complement cascade proteins.

17. The method of claim 16, wherein the binding of a coat protein or derivative to specific complement cascade proteins is tested using an overlay blot assay.

18. The method of claim 16, wherein the coat protein or derivative is further identified by the ability of said coat protein or derivative to form oligomers.

19. The method of claim 18, wherein said coat protein or derivative form dimers.

20. The method of claim 18, wherein said coat proteins or derivative form trimers.

21. The method of claim 1, wherein the levels of complement cascade protein iC3b is measured.

22. The method of claim 1, wherein the coat protein or derivative inhibits the formation of iC3b protein.

* * * * *